United States Patent
Malefyt et al.

(10) Patent No.: US 10,653,699 B2
(45) Date of Patent: May 19, 2020

(54) CONTROLLED-RELEASE TOZADENANT FORMULATIONS

(71) Applicant: BIOTIE THERAPIES, INC., South San Francisco, CA (US)

(72) Inventors: Thomas R. Malefyt, Carmel Valley, CA (US); Christopher G. Salentine, San Rafael, CA (US); Mehdi Paborji, Cupertino, CA (US); Stephen I. Bandak, San Francisco, CA (US)

(73) Assignee: Biotie Therapies, Inc., Ardsley, NY (US)

( * ) Notice: Subject to any disclaimer, the term of this patent is extended or adjusted under 35 U.S.C. 154(b) by 0 days.

(21) Appl. No.: 15/737,993

(22) PCT Filed: May 23, 2016

(86) PCT No.: PCT/US2016/033787
§ 371 (c)(1),
(2) Date: Dec. 19, 2017

(87) PCT Pub. No.: WO2016/204939
PCT Pub. Date: Dec. 22, 2016

(65) Prior Publication Data
US 2018/0303843 A1    Oct. 25, 2018

Related U.S. Application Data

(60) Provisional application No. 62/182,121, filed on Jun. 19, 2015.

(51) Int. Cl.
*A61K 31/5377* (2006.01)
*A61K 9/20* (2006.01)
(Continued)

(52) U.S. Cl.
CPC ........ *A61K 31/5377* (2013.01); *A61K 9/2018* (2013.01); *A61K 9/2054* (2013.01);
(Continued)

(58) Field of Classification Search
CPC .......................... A61K 31/5377; A61K 31/198
See application file for complete search history.

(56) References Cited

U.S. PATENT DOCUMENTS

| | | | |
|---|---|---|---|
| 7,368,446 B2 | 5/2008 | Flohr et al. | |
| 2005/0197385 A1 | 9/2005 | Scheller et al. | |

(Continued)

FOREIGN PATENT DOCUMENTS

| | | |
|---|---|---|
| CA | 2567703 | 12/2005 |
| CN | 101543497 | 9/2009 |

(Continued)

OTHER PUBLICATIONS

U.S. Appl. No. 13/882,132, "Non-Final Office Action", dated Jun. 25, 2018, 14 pages.
(Continued)

*Primary Examiner* — San Ming R Hui
(74) *Attorney, Agent, or Firm* — Kilpatrick Townsend & Stockton LLP (57) ABSTRACT

The present invention provides a controlled-release composition containing tozadenant, at least one cellulose ether, and one or more pharmaceutically acceptable excipients. In the composition, the tozadenant is present in an amount ranging from about 30% (w/w) to about 65% (w/w) based on the total composition weight; and the cellulose ether is present in an amount sufficient to provide: not less than about 10% and not more than about 30% tozadenant dissolution over a 2-hour test period, not less than about 55% tozadenant dissolution over a 10-hour test period, and not less than about 80% tozadenant dissolution over a 16-hour test period.

(Continued)

Use of the composition for treatment of Parkinson's disease is also described.

34 Claims, 2 Drawing Sheets

(51) Int. Cl.
    *A61K 31/198*     (2006.01)
    *A61P 25/16*     (2006.01)
(52) U.S. Cl.
    CPC ............ *A61K 31/198* (2013.01); *A61P 25/16* (2018.01); *A61K 2300/00* (2013.01)

(56) References Cited

U.S. PATENT DOCUMENTS

| | | | |
|---|---|---|---|
| 2005/0261289 A1* | 11/2005 | Flohr | C07D 417/12 514/233.5 |
| 2005/0267085 A1 | 12/2005 | Di Paolo et al. | |
| 2006/0178379 A1 | 8/2006 | Kase et al. | |
| 2007/0059365 A1 | 3/2007 | Pollock et al. | |
| 2010/0255099 A1 | 10/2010 | Kim et al. | |
| 2011/0003870 A1 | 1/2011 | Vieira et al. | |
| 2012/0165323 A1* | 6/2012 | Dodd | A01N 25/14 514/226.5 |
| 2013/0317019 A1 | 11/2013 | Bandak et al. | |

FOREIGN PATENT DOCUMENTS

| | | | |
|---|---|---|---|
| CN | 107281491 | 10/2017 | |
| EP | 0 468 392 A1 | 7/1991 | |
| EP | 2799065 A1 * | 11/2014 | ........... A61K 9/2077 |
| EP | 3310344 | 4/2018 | |
| IL | 225868 | 8/2019 | |
| IN | 4068DELNP2013 | 11/2014 | |
| JP | H04-234316 A | 8/1992 | |
| JP | 2000-511170 A | 8/2000 | |
| JP | 2005523898 | 8/2005 | |
| JP | 2008500295 | 1/2008 | |
| JP | 2017019829 | 1/2017 | |
| JP | 6315991 | 4/2018 | |
| JP | 644951 B2 | 12/2018 | |
| JP | 6444951 | 12/2018 | |
| KR | 101955045 | 2/2019 | |
| MX | 2013005014 | 1/2014 | |
| NZ | 729564 | 1/2019 | |
| WO | 97/45124 A1 | 12/1997 | |
| WO | 2003063876 | 8/2003 | |
| WO | 2005116026 | 12/2005 | |
| WO | 2010148121 | 12/2010 | |
| WO | 2012061787 | 5/2012 | |
| WO | 2014/066681 A1 | 5/2014 | |
| WO | 2016204939 | 12/2016 | |

OTHER PUBLICATIONS

U.S. Appl. No. 13/882,132 , "Restriction Requirement", dated Mar. 25, 2014, 11 pages.
JP2016-164379 , "Office Action", dated Jun. 13, 2017, 5 pages.
"SYN-115", Thomson Reuters Integrity Available on internet at : http://integrity.thomson-pharma.com, Dec. 16, 2005, 1 page.
"Synosia Therapeutics' SYN-115 Improves Motor and Non-Motor Function in Patients with Mild-to-Moderate Parkinson's Disease", Available Online at:—http://www.businesswire.com/news/home/20100414005078/en/Synosia-Therapeutics%E2%80%99-SYN-115-Improves-Motor-Non-Motor-Function, Apr. 14, 2010, 3 pages.
"Synosia's SYN-115 Demonstrates Clinical Benefit in Parkinson's Disease", Available online at:—https://www.drugs.com/clinical_trials/synosia-s-syn-115-demonstrates-clinical-benefit-parkinson-s-9158.html, Apr. 14, 2010, 2 pages.
U.S. Appl. No. 13/882,132 , "Final Office Action", dated Jul. 25, 2016, 12 pages.
U.S. Appl. No. 13/882,132 , "Final Office Action", dated Dec. 6, 2017, 16 pages.
U.S. Appl. No. 13/882,132 , "Final Office Action", dated Jun. 10, 2015, 9 pages.
U.S. Appl. No. 13/882,132 , "Non Final Office Action", dated Mar. 29, 2017, 14 pages.
U.S. Appl. No. 13/882,132 , "Non Final Office Action", dated Sep. 4, 2014, 9 pages.
U.S. Appl. No. 13/882,132 , "Non-Final Office Action", dated Nov. 5, 2015, 9 pages.
PCT/US2016/033787 , "International Search Report and Written Opinion", dated Aug. 5, 2016, 11 pages.
AU2011323152 , "First Examiner Report", dated Mar. 3, 2016, 4 pages.
Bertorelli et al., Drug Development Research, vol. 37, 1996, pp. 65-72.
Black et al., "A Randomized, Double-Blind, Placebo-Controlled Cross-Over Trial of the Adenosine 2a Antagonist SYN115 in Parkinson Disease", Neurology, vol. 74, No. 9, Suppl. 2, Mar. 2010 (Mar. 2010), 62nd Annual Meeting of the American-Academy-Of-Neurology; Toronto, Canada, Mar. 2010, p. A317.
Bove et al., "Adenosine A2A antagonism reverses levodopa-induced motor alterations in hemiparkinsonian rats", Synapse, vol. 46, Issue 4, Dec. 15, 2002, pp. 251-257.
Businesswire , "Synosia therapeutics' SYN-115 improves motor and non-motor function in patients with mild-to moderate Parkinson's disease", www.businesswire.com/news/home, Apr. 14, 2010.
CN201180053445.0 , "Office Action", dated Aug. 19, 2015, 11 pages.
CN201180053445.0 , "Office Action", dated Jun. 7, 2016, 12 pages.
CN201180053445.0 , "Office Action", dated Mar. 20, 2017, 14 pages.
CN201180053445.0 , "Office Action", dated Sep. 28, 2014, 8 pages.
Dickerson et al., "The adenosine 2a antagonist SYN115 decreases thalamic rCBF in Parkinson disease", Society for Neuroscience Abstract Viewer and Itinerary Planner, vol. 39,2009, & 39th Annual Meeting of the Society-For-Neuroscience, Oct. 17-21, 2009.
drugs.com , "Synosia's SYN-115 demonstrates clinical benefit in Parkinson's disease", www.drugs.com/clinical_trials, Apr. 14, 2010, 2 pages.
EA201390653 , "Office Action", dated Oct. 26, 2015, 4 pages.
EA201390653 , "Office Action", dated Feb. 10, 2015, 6 pages.
EP11838922.0 , "Extended European Search Report", dated Apr. 24, 2014, 10 Pages.
EP11838922.0 , "Office Action", dated Jun. 29, 2017, 4 pages.
EP11838922.0 , "Office Action", dated May 11, 2016, 5 pages.
Haslinger et al., "Brain", Event-related functional magnetic resonance imaging in Parkinson's disease before and after levodopa., 2001, pp. 558-570.
Hauser et al., "Study of istradefylline in patients with Parkinson's disease on levodopa with motor fluctuations", Movement Disorders, vol. 23, No. 15, 2008, pp. 2177-2185.
Hou , "PD Cognitive Impairment", Shandong Medical Journal, vol. 49, Issue 31, Dec. 2009, pp. 107-108.
IL225868 , "Office Action", dated Feb. 3, 2016, 3 pages.
IL225868 , "Office Action", dated Jun. 11, 2017, 3 pages.
Jacobson et al., "Adenosine receptors as therapeutic targets", Nature Reviews: Druq Discovery, vol. 5, No. 3, Mar. 2006, pp. 247-264.
JP2013-537896 , "Office Action", dated Jul. 11, 2017, 28 pages.
JP2013-537896 , "Office Action", dated Sep. 1, 2015, 7 pages.
JP2013-537896 , "Office Action", dated Apr. 26, 2016, 8 pages.
KR10-2013-7014385 , "Office Action", dated Sep. 20, 2017, 12 pages.
Lange et al., "Dopaminergic effects on cognitive performance in patients with Parkinson's disease", J Neural Transm Suppl., vol. 46, Dec. 31, 1995, pp. 423-432.
Leiva-Santana et al., "Levodopa and cognitive disorders in Parkinson's disease", Revista de Neurología., vol. 43, No. 2, Jul. 16, 2006, pp. 95-100.
Lewitt et al., "Adenosine A2A receptor antagonist istradefylline (KW-6002) reduces "off" time in Parkinson's disease: a double-blind, randomized, multicenter clinical trial (6002-US-005)", Annals of Neurology, vol. 63, No. 3, Mar. 2008, pp. 295-302.

(56) References Cited

OTHER PUBLICATIONS

MX/a/2013/005014, "Office Action", dated Nov. 26, 2015.
MX/a/2013/005014, "Office Action", dated Feb. 22, 2017, 10 pages.
MX/a/2013/005014, "Office Action", dated Oct. 24, 2017, 19 pages.
MX/a/2013/005014, "Office Action", dated Jun. 20, 2016, 4 pages.
NZ609803, "First Examiner Report", dated Feb. 13, 2014, 2 pages.
NZ710876, "First Examiner Report", dated Aug. 28, 2015, 3 pages.
NZ729564, "First Examiner Report", dated Mar. 20, 2017, 3 Pages.
PCT/US10/55681, "International Search Report and Written Opinion", dated Jan. 7, 2011, 6 pages.
PCT/US11/59466, "International Search Report and Written Opinion", dated Mar. 12, 2012, 6 pages.
PCT/US2016/033787, "International Preliminary Report on Patentability", dated Dec. 28, 2017, 7 pages.
Rezak et al., "Current Pharmacotherapeutic Treatment Options in Parkinson's Disease", Disease-AMONTH, Year Book Publ., Chicago, IL, US, vol. 53, No. 4, Apr. 1, 2007, pp. 214-222.
Sanchez-Castaneda et al., "Cognitive improvement after duodenal levodopa infusion in cognitively impaired Parkinson's disease patients", Progress in Neuro-Psychopharmacology & Biological Psychiatry, Elsevier, GB; vol. 34, No. 1, Feb. 1, 2010, pp. 250-251.
Simola et al., "Adenosine A2A receptor antagonists and Parkinson's disease: state of the art and future directions", Current Pharmaceutical Design, vol. 14, No. 15, 2008, pp. 1475-1489.
Stacy et al., "A 12-week, placebo-controlled study (6002-US-006) of istradefylline in Parkinson disease", Neurology, vol. 70, No. 23, Jun. 3, 2008, pp. 2233-2240.
Takahashi et al., "Adenosine receptor antagonists for cognitive dysfunction: a review of animal studies", Frontiers in Bioscience, vol. 13, Jan. 1, 2008, pp. 2614-2632.
Tedrus et al., "Dementia and Mild Cognitive Impairment in Patients With Parkinson's Disease", Arq Neuropsiquiatr, vol. 67, Dec. 2009, pp. 423-427.
AU2017201446, "Second Examination Report", dated Jan. 3, 2019, 5 pages.
Bjorness et al., "Adenosine and Sleep", Curr Neuropharmacol., vol. No. 7, Issue No. 3, Sep. 2009, pp. 238-245.
U.S. Appl. No. 13/882,132, "Final Office Action", dated Jan. 30, 2019, 14 pages.
Contin et al., "Pharmacokinetic Optimisation in the Treatment of Parkinson's Disease", Clinical Pharmacokinetics, vol. 30, No. 6, Jun. 1996, pp. 463-481.
Emre, "Practical Guidance for the Management of Parkinson's Disease with Levodopa", Proceedings of the Neuronet-PD Working Group, vol. 9, No. 2, May-Jun. 2009, 4 pages.
Novak et al., "Drug-Induced Sleep Disturbances Focus on Nonpsychotropic Medications", Drug Saf., vol. 16, No. 2, Feb. 1997, 17 pages.
Okereke, "Role of Integrative Pharmacokinetic and Pharmacodynamic Optimization Strategy in the Management of Parkinson's Disease Patients Experiencing Motor Fluctuations withLevodopa", Journal of Pharmacy & Pharmaceutical Sciences, vol. 5, No. 2, Jun. 24, 2002, 16 pages.
"Safety and Tolerability of Tozadenant as Adjunctive Therapy in Levodopa-Treated Patients With Parkinson's Disease", ClinicalTrials.gov, Avalable online at : https://clinicaltrials.gov/ct2/show/NCT03051607, Accessed from Internet on Sep. 9, 2019, 36 pages.
"Synosia Therapeutics' SYN-115 Demonstrates Clinical Benefit in Parkinson's Disease", Available online at: http://www.drugs.com/clinical_trials/synosia-s-syn-115-demonstrates-clinical-benefit-parkinson-s-9158.html, Apr. 2010, 3 pages.
AU2017201446, "First Examination Report", dated Jan. 3, 2018, 6 pages.
AU2018286608, "First Examination Report", dated Aug. 6, 2019, 4 pages.
AU2018286608, "Second Examination Report", dated Nov. 22, 2019, 3 pages.
CA2,816,834, "Office Action", dated Jul. 10, 2019, 3 pages.
CA2,816,834, "Office Action", dated Nov. 8, 2017, 3 pages.
CN201180053445.0, "Office Action", dated May 23, 2018, 7 pages.
EP11838922.0, "Office Action", dated Aug. 17, 2018, 4 pages.
IL225868, "Notice of Allowance", dated Jan. 30, 2019, 3 pages.
IN4068/DELNP/2013, "First Examination Report", dated Feb. 9, 2018, 7 pages.
JP2013-537896, "Notice of Allowance", dated Feb. 27, 2018, 2 pages.
JP2013-537896, "Office Action", dated Jun. 13, 2017, 5 pages.
JP2016-164379, "Notice of Decision to Grant", dated Oct. 30, 2018, 5 pages.
JP2016-164379, "Office Action", dated May 22, 2018, 6 pages.
JP2018-221977, "Notice of Decision to Grant", dated Oct. 1, 2019, 5 pages.
KR10-2013-7014385, "Notice of Decision to Grant", dated Dec. 5, 2018, 2 pages.
KR10-2013-7014385, "Office Action", dated May 24, 2018, 4 pages.
KR10-2019-7005483, "Office Action", dated May 8, 2019, 4 pages.
KR10-2019-7005483, "Office Action", dated Nov. 13, 2019, 6 pages.
NZ729564, "Notice of Allowance", dated Sep. 26, 2018, 1 page.
NZ746118, "First Examiner Report", dated Sep. 26, 2018, 2 pages.
PCT/US2010/055681, "International Preliminary Report on Patentability", dated May 16, 2013, 6 pages.
PCT/US2011/059466, "International Preliminary Report on Patentability", dated May 16, 2013, 6 pages.
The International Search Report and Written Opinion received in the corresponding International Application No. PCT/US2016/033787, dated Dec. 22, 2016.
Hogan, J., "Hydroxypropylmethylcellulose Sustained Release Technology", Drug Development and Industrial Pharmacy, vol. 15, No. 6, 1989, pp. 975-999.
U.S. Appl. No. 13/882,132, "Non-Final Office Action", dated Aug. 13, 2019, 13 pages.
EP16727086.7, "Office Action", dated Jul. 17, 2019, 5 pages.
Pinna, A., "Adenosine $A_{2A}$ Receptor Antagonists in Parkinson's Disease: Progress in Clinical Trials from the Newly Approved Istradefylline to Drugs in Early Development and Those Already Discontinued," CNS Drugs 2014 28:455-474.
Vilar, et al., "Polymers and Drug Delivery Systems," Current Drug Delivery, 2012, 9, 367-394.
Nokhodehi, et al., "The Role of Oral Controlled Release Matrix Tablets in Drug Delivery Systems," BioImpacts, 2012, 2(4), 175-187.
EP App No. 16727086.7, "Exam Report," dated Mar. 5, 2020, 5 pages.
"Isomalt", International Pharmaceutical Excipients Council Japan Ed., Revised Handbook of Pharmaceutical Excipients, Yakuji Nippo, Limited, 2007, pp. 96-101.
JP App No. 2018-518564, "Office Action," dated Mar. 19, 2020, 5 pages.

* cited by examiner

CONTROLLED-RELEASE TOZADENANT FORMULATIONS

CROSS-REFERENCE TO RELATED APPLICATIONS

This application claims the benefit of U.S. Provisional Application No. 62/182,121 (filed Jun. 19, 2015). This application is incorporated by reference in its entirety for all purposes.

BACKGROUND OF THE INVENTION

Tozadenant is an adenosine $A_{2A}$ receptor antagonist that has demonstrated efficacy in treating Parkinson's disease and other conditions affecting the central nervous system. Tozadenant can be used as an adjunct to levodopa in patients with Parkinson's disease who are experiencing end-of-dose wearing-off (motor fluctuations). This promising activity is limited by side effects associated with administration of tozadenant, which include dyskinesias, dizziness, nausea, flushing, and transient hypertension. Accordingly, new formulations are needed to realize the full benefit of tozadenant in levodopa-based treatment of Parkinson's disease and other therapeutic applications. The present invention provides new tozadenant formulations that meet this need.

BRIEF SUMMARY OF THE INVENTION

In one aspect, the invention provides a composition containing tozadenant, at least one cellulose ether, and one or more pharmaceutically acceptable excipients. In the composition, the tozadenant is present in an amount ranging from about 30% (w/w) to about 65% (w/w) based on the total composition weight; and the cellulose ether is present in an amount sufficient to provide: not less than about 10% and not more than about 30% tozadenant dissolution over a 2-hour test period, not less than about 55% tozadenant dissolution over a 10-hour test period, and not less than about 80% tozadenant dissolution over a 16-hour test period.

In some embodiments, the test period comprises stirring the composition with paddles at 100 rpm in a test solution containing 0.1 M hydrochloric acid and 1% (w/w) sodium dodecylsulfate, and the ratio of the test solution to the total composition is about 1800/1 (w/w).

In some embodiments: the cellulose ether is present in an amount ranging from about 22% (w/w) to about 27% (w/w) based on the total composition weight; the cellulose ether consists essentially of hydroxypropyl methylcellulose; and the hydroxypropyl methylcellulose is characterized by an apparent viscosity ranging from about 60 cP to about 140 cP when formulated as a 2% (w/w) solution in water at 20° C.

In some embodiments, the cellulose ether is present in an amount ranging from about 15% (w/w) to about 30% (w/w) based on the total composition weight; the cellulose ether consists essentially of hydroxypropyl methylcellulose; and the hydroxypropyl methylcellulose is characterized by an apparent viscosity ranging from about 2800 cP to about 5800 cP when formulated as a 2% (w/w) solution in water at 20° C.

In a related aspect, the invention provides a composition containing tozadenant, at least one cellulose ether, and one or more pharmaceutically acceptable excipients. The tozadenant is present in the composition in an amount sufficient to, when the composition is administered orally once a day for at least 14 days, provide a tozadenant steady-state concentration ($C_{ss}$) that is equivalent to the $C_{ss}$ obtained from immediate-release formulations that are therapeutically effective when administered more than once-daily. In some embodiments, the $C_{ss}$ is in the range of about 1.0-4.0 µg/mL. The cellulose ether is present in the composition in an amount sufficient to provide a tozadenant maximum concentration ($C_{max}$) below a threshold that results in an unacceptable incidence or severity of adverse events when the composition is administered orally once a day for at least 14 days. In some embodiments, the $C_{max}$ threshold is in the range of about 2.0-5.0 µg/mL.

In another aspect, the invention provides a method for treating Parkinson's disease. The method includes administering a therapeutically effective amount of levodopa and a therapeutically effective amount of a tozadenant composition according to the invention to a patient in need thereof. In some embodiments, the tozadenant composition is administered in an amount sufficient to reduce levodopa off-time.

DETAILED DESCRIPTION OF THE INVENTION

I. General

The present invention provides tozadenant formulations having dissolution profiles that give rise to favorable pharmacokinetic parameters and reduced side effects when administered orally to Parkinson's disease patients.

II. Definitions

The terms "tozadenant" and "SYN115" refer to 4-hydroxy-4-methyl-piperidine-1-carboxylic acid (4-methoxy-7-morpholin-4-yl-benzothiazol-2-yl)-amide according to Formula I:

and pharmaceutically acceptable salts and hydrates thereof. Tozadenant and uses thereof are described in U.S. Pat. No. 7,368,446 and U.S. patent application Ser. No. 13/882,132, which are incorporated herein by reference in their entirety.

The term "cellulose ether" refers to a polymeric carbohydrate according to Formula II, having a backbone consisting of β(1→4) linked D-glucose subunits:

(II)

In cellulose ethers according to Formula II, each R group is independently selected from H, $C_{1-6}$ alkyl, hydroxy-($C_{1-6}$ alkyl), and carboxy-($C_{1-6}$ alkyl); and n is an integer ranging from 50 about to about 2000. Examples of cellulose ethers include, but are not limited to, methylcellulose and hydroxypropyl methylcellulose.

The term "hydroxypropyl methylcellulose" refers to a cellulose ether according to Formula II, wherein each R group is independently selected from H, methyl (i.e., —$CH_3$), and 2-hydroxypropyl (i.e., —$CH_2$—CH(OH)—$CH_3$).

The term "viscosity" refers to the internal friction of a fluid that results in resistance to forces associated with the movement of the fluid. Viscosity is frequently expressed using the poise unit (P), one poise being equal to 1 gm·$cm^{-1}·s^{1}$. A centipoise (cP) is one one-hundredth of one poise. "Apparent viscosity" refers to the viscosity of a fluid containing a specific solute at a specified concentration, measured at a specified temperature. Methods for measuring viscosity are known in the art.

The term "pharmaceutically acceptable excipient" refers to a substance that aids the administration of an active agent to a subject. By "pharmaceutically acceptable," it is meant that the excipient is compatible with the other ingredients of the formulation and is not deleterious to the recipient thereof. Pharmaceutical excipients useful in the present invention include, but are not limited to, binders, fillers, disintegrants, lubricants, glidants, coatings, sweeteners, flavors and colors.

The term "weight percent," expressed as % (w/w), refers to the ratio of the weight of a particular component in a mixture to the total weight of the mixture multiplied by 100. As a non-limiting example, a composition with a total weight of 5 g containing 1 g of tozadenant can be expressed as 20% (w/w) tozadenant.

The term "percent dissolution," expressed as % dissolution, refers to the ratio of the amount of a substance dissolved in a solution, wherein the substance in the solution results from exposure of a solid mixture containing the substance to the solution, and the amount of the component in the solid mixture, multiplied by 100. As a non-limiting example, a solution having 0.5 g dissolved tozadenant resulting from combination of a buffer with a solid composition containing 1 gram of tozadenant amounts to 50% tozadenant dissolution.

The term "$C_{max}$" refers to the maximum concentration of a substance (e.g., tozadenant) in the blood stream or other physiological compartment of a subject during or after administration of the substance to the subject. Cmax will depend, in part, on factors including the dose of the substance and the particular formulation administered to the subject. The time $t_{max}$ during or after administration at which $C_{max}$ is reached will depend, in part, on factors including the formulation administered to the subject and the rate of elimination of the substance from the subject. Methods for determining $C_{max}$, $t_{max}$, and other pharmacokinetic parameters are known in the art.

The term "test period" refers to a defined period of time during a dissolution test procedure wherein a solid composition containing tozadenant is exposed to a fluid under specified conditions. Dissolution can be determined by an in vitro laboratory test known in the art. Test procedures are described, for example, in various pharmacopeia such as United States Pharmacopeia Chapter <711> and European Pharmacopeia Section 2.9.3. The dissolution test procedure can include the use of fluids having specific components (e.g., surfactants or buffers in specified amounts) in specified quantities (e.g., particular fluid-to-solid ratios) at particular temperatures with specific apparatuses (e.g., stirring paddles, sinkers, and the like).

The term "Parkinson's disease" refers to a clinical syndrome marked by a variety of motor symptoms, which may include, e.g., tremor at rest; rigidity, bradykinesia, and deficiency of postural reflexes. The syndrome is associated with degeneration of the basal ganglia of the brain and a deficiency of the neurotransmitter dopamine.

The term "treating" refers to any indicia of success in the treatment or amelioration of an injury, pathology, condition, or symptom (e.g., pain), including any objective or subjective parameter such as abatement, remission, diminishing of symptoms; or making the symptom, injury, pathology or condition more tolerable to the patient; and decreasing the frequency or duration of the symptom or condition. The treatment or amelioration of symptoms can be based on any objective or subjective parameter; including, e.g., the result of a physical examination.

The term "administering," unless otherwise specified, refers to oral administration of a substance or composition to a subject.

The term "subject" refers to animals such as mammals, including, but not limited to, primates (e.g., humans), cows, sheep, goats, horses, dogs, cats, rabbits, rats, mice and the like.

The term "therapeutically effective amount" refers to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); Goodman & Gilman's *The Pharmacological Basis of Therapeutics*, 11th Edition, 2006, Brunton, Ed., McGraw-Hill; and *Remington: The Science and Practice of Pharmacy*, 21st Edition, 2005, Hendrickson, Ed., Lippincott, Williams & Wilkins).

The term "levodopa" refers to (−)-3-(3,4-dihydroxyphenyl)-L-alanine (identifiable by CAS Registry No. 59-92-7).

The term "levodopa off-time" refers to the period following a dose of levodopa when Parkinson's disease symptoms (including, but not limited to, tremor, bradykinesia, and rigidity) may return and persist until another dose of levodopa is administered.

The terms "about" and "around," as used herein to modify a numerical value, indicate a close range surrounding that explicit value. If "X" were the value, "about X" or "around X" would indicate a value from 0.8X to 1.2X, preferably a value from 0.9X to 1.1X, and, more preferably, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

III. Controlled-Release Tozadenant Formulations

In one aspect, the invention provides a composition containing tozadenant, at least one cellulose ether, and one or more pharmaceutically acceptable excipients. In the composition, the tozadenant is present in an amount ranging from about 30% (w/w) to about 65% (w/w) based on the total composition weight; and the cellulose ether is present in an amount sufficient to provide: not less than about 10% and not more than about 30% tozadenant dissolution over a 2-hour test period, not less than about 55% tozadenant dissolution over a 10-hour test period, and not less than about 80% tozadenant dissolution over a 16-hour test period.

In some embodiments, the cellulose ether is present in an amount sufficient to provide: not less than about 10% and not more than about 30% tozadenant dissolution over a 2-hour test period, not less than about 35% and not more than about 75% tozadenant dissolution over a 6-hour test period, not less than about 55% tozadenant dissolution over a 10-hour test period, and not less than about 80% tozadenant dissolution over a 16-hour test period.

The compositions of the invention provide extended release of tozadenant when administered orally to patients. The modified release profiles resulting from the formulations are associated with a number of advantages in the treatment of neurological conditions such as Parkinson's disease, including the reduction of side effects such as dyskinesias, nausea, dizziness, flushing, and transient hypertension.

The compositions of the invention are characterized by gradual dissolution of tozadenant, occurring over several hours when the compositions are exposed to gastric fluid, buffer solutions, or other experimental or physiological liquid media. The compositions are typically formulated so as to prevent rapid dissolution of tozadenant. In general, not more than about 15% of the tozadenant in the composition will dissolve over a 1-hour period after administration to a patient or over a 1-hour laboratory test period. For example, compositions can be formulated to provide not less than about 3% and not more than about 15% tozadenant dissolution over a 1-hour test period (i.e., about 8-15% tozadenant dissolution over a 1-hour test period). Compositions can be formulated to provide about 4-6%, or about 6-8%, or about 8-10%, or about 10-12%, or about 12-15% tozadenant dissolution over a 1-hour test period. Compositions can be formulated to provide about 9-14%, or about 10-13%, or about 11-12% tozadenant dissolution over a 1-hour test period. Compositions can be formulated to provide not more than about 4, 5, 6, 7, 8, 9, 10, 11, 12, 13, 14, or 15% tozadenant dissolution over a 1-hour test period. Compositions can be formulated to provide not less than about 3, 4, 5, 6, 7, 8, 9, 10, 11, 12, 13, or 14% tozadenant dissolution over a 1-hour test period.

Dissolution of tozadenant progresses with continued exposure of a composition to a liquid medium. Typically, compositions of the invention are formulated such that about 10-30% tozadenant dissolves over a 2-hour test period. Compositions can be formulated to provide about 10-12%, or about 12-14%, or about 14-16%, or about 16-18%, or about 18-20%, or about 20-22%, or about 22-24%, or about 24-26%, or about 26-28%, or about 28-30% tozadenant dissolution over a 2-hour test period. Compositions can be formulated to provide about 11-27%, or about 12-26%, or about 13-25%, or about 14-24%, or about 15-23%, or about 16-22%, or about 17-21%, or about 18-20% tozadenant dissolution over a 2-hour test period.

Compositions can be formulated to provide about 11, 12, 13, 14, 15, 16, 17, 18, 19, 20, 21, 22, 23, 24, 25, 26, 27, 28, 29, or 30% tozadenant dissolution over a 2-hour test period. Compositions can be formulated to provide not more than about 12, 13, 14, 15, 16, 17, 18, 19, 20, 21, 22, 23, 24, 25, 26, 27, 28, 29, or 30% tozadenant dissolution over a 2-hour test period. Compositions can be formulated to provide not less than about 11, 12, 13, 14, 15, 16, 17, 18, 19, 20, 21, 22, 23, 24, 25, 26, 27, 28, or 29% tozadenant dissolution over a 2-hour test period.

Compositions of the invention can be formulated such that about 20-60% tozadenant dissolves over a 4-hour test period. Compositions can be formulated to provide about 20-22%, or about 22-24%, or about 24-26%, or about 26-28%, or about 28-30%, or about 30-32%, or about 32-34%, or about 34-36%, or about 36-38%, or about 38-40%, or about 40-42%, or about 42-44%, or about 44-46%, or about 46-48%, or about 48-50%, or about 50-52%, or about 52-56%, or about 56-60% tozadenant dissolution over a 4-hour test period. Compositions can be formulated to provide about 21-58%, or about 22-55%, or about 23-49%, or about 24-48%, or about 25-47%, or about 26-46%, or about 27-45%, or about 28-44%, or about 29-43%, or about 30-42%, or about 31-41%, or about 32-40%, or about 33-39%, or about 34-38%, or about 35-37% tozadenant dissolution over a 4-hour test period.

Compositions can be formulated to provide about 20, 22, 24, 26, 28, 30, 32, 34, 36, 38, 40, 42, 44, 46, 48, 50, 52, 54, 56, 58, or 60% tozadenant dissolution over a 4-hour test period. Compositions can be formulated to provide not more than about 22, 24, 26, 28, 30, 32, 34, 36, 38, 40, 42, 44, 46, 48, 50, 52, 54, 56, 58, or 60% tozadenant dissolution over a 4-hour test period. Compositions can be formulated to provide not less than about 20, 22, 24, 26, 28, 30, 32, 34, 36, 38, 40, 42, 44, 46, 48, 50, 52, 54, 56, or 58% tozadenant dissolution over a 4-hour test period.

Compositions of the invention can be formulated such that about 30-80% tozadenant dissolves over a 6-hour test period. Compositions can be formulated to provide about 30-34%, or about 34-39%, or about 39-44%, or about 44-49%, or about 49-54%, or about 54-59%, or about 59-64%, or about 64-69%, or about 69-74%, or about 74-77%, or about 77-80% tozadenant dissolution over a 6-hour test period. Compositions can be formulated to provide about 32-77%, or about 35-72%, or about 38-68%, or about 41-65%, or about 44-62%, or about 47-59%, or about 50-56% tozadenant dissolution over a 6-hour test period.

Compositions can be formulated to provide about 30, 32, 35, 38, 41, 44, 47, 50, 53, 56, 59, 62, 65, 68, 71, 74, 77, or 80% tozadenant dissolution over a 6-hour test period. Compositions can be formulated to provide not more than about 32, 35, 38, 41, 44, 47, 50, 53, 56, 59, 62, 65, 68, 71, 74, 77, or 80% tozadenant dissolution over a 6-hour test period. Compositions can be formulated to provide not less than about 29, 32, 35, 38, 41, 44, 47, 50, 53, 56, 59, 62, 65, 68, 71, 74, or 77% tozadenant dissolution over a 6-hour test period.

Compositions of the invention can be formulated such that about 40-95% tozadenant dissolves over an 8-hour test period. Compositions can be formulated to provide about 40-44%, or about 44-49%, or about 49-54%, or about 54-59%, or about 59-64%, or about 64-69%, or about 69-74%, or about 74-79%, or about 79-84%, or about 84-89%, or about 89-95% tozadenant dissolution over an 8-hour test period. Compositions can be formulated to provide about 42-93%, or about 45-90%, or about 48-87%, or about 51-84%, or about 54-81%, or about 57-78%, or about 60-75%, or about 63-72%, or about 66-69% tozadenant dissolution over an 8-hour test period.

Compositions can be formulated to provide about 40, 42, 45, 48, 51, 54, 57, 60, 63, 66, 69, 72, 75, 78, 81, 84, 87, 90, 93, or 95% tozadenant dissolution over an 8-hour test period. Compositions can be formulated to provide not more than about 42, 45, 48, 51, 54, 57, 60, 63, 66, 69, 72, 75, 78, 81, 84, 87, 90, 93, or 95% tozadenant dissolution over an 8-hour test period. Compositions can be formulated to provide not less than about 40, 42, 45, 48, 51, 54, 57, 60, 63, 66, 69, 72, 75, 78, 81, 84, 87, 90, or 93% tozadenant dissolution over an 8-hour test period.

Compositions of the invention can be formulated such that about 55-99% tozadenant dissolves over a 10-hour test period. Compositions can be formulated to provide about 55-58%, or about 58-63%, or about 63-68%, or about 68-73%, or about 73-78%, or about 78-83%, or about 83-88%, or about 88-95% tozadenant dissolution over a 10-hour test period. Compositions can be formulated to provide about 55-90%, or about 57-87%, or about 60-84%, or about 63-81%, or about 66-78%, or about 69-75% tozadenant dissolution over a 10-hour test period.

Compositions can be formulated to provide about 55, 57, 60, 63, 66, 69, 72, 75, 78, 81, 84, 87, 90, 93, 96, or 99% tozadenant dissolution over a 10-hour test period. Compositions can be formulated to provide not more than about 57, 60, 63, 66, 69, 72, 75, 78, 81, 84, 87, 90, 93, 96, or 99% tozadenant dissolution over a 10-hour test period. Compositions can be formulated to provide not less than about 55, 57, 60, 63, 66, 69, 72, 75, 78, 81, 84, 87, 90, 93, or 96% tozadenant dissolution over a 10-hour test period.

Compositions of the invention can be formulated such that about 60-99% tozadenant dissolves over a 12-hour test period. Compositions can be formulated to provide about 60-63%, or about 63-68%, or about 68-73%, or about 73-78%, or about 78-83%, or about 83-88%, or about 88-93%, or about 93-99% tozadenant dissolution over a 12-hour test period. Compositions can be formulated to provide about 62-98%, or about 64-91%, or about 67-88%, or about 70-85%, or about 73-82%, or about 76-79% tozadenant dissolution over a 12-hour test period.

Compositions can be formulated to provide about 60, 64, 67, 70, 73, 76, 79, 82, 85, 88, 91, 94, or 99% tozadenant dissolution over a 12-hour test period. Compositions can be formulated to provide not more than about 64, 67, 70, 73, 76, 79, 82, 85, 88, 91, 94, or 99% tozadenant dissolution over a 12-hour test period. Compositions can be formulated to provide not less than about 60, 61, 64, 67, 70, 73, 76, 79, 82, 85, 88, 91, or 94% tozadenant dissolution over a 12-hour test period.

Compositions of the invention are generally formulated to provide not less than about 80% tozadenant dissolution over a 16-hour test period. Compositions can be formulated to provide about 85-90%, about 90-95%, or greater than about 95% tozadenant dissolution over a 16-hour test period. Compositions can be formulated to provide not less than about 85, 86, 87, 88, 90, 91, 92, 93, 94 or 95% tozadenant dissolution over a 16-hour test period.

Dissolution can be assessed using any suitable test conditions. For example, laboratory dissolution tests can be conducted using acidic or alkaline aqueous media. Dissolution media can be formulated to simulate gastric fluid or intestinal fluid and can include enzymes, such as pepsin and pancreatin, as well as detergents and solubilizers including ionic surfactants, non-ionic surfactants, lecithin, lysolecithin, bile salts, mono glycerides, and fatty acids. Mixed micelles containing amphiphilic species such as sodium taurocholate and lecithin can be used to simulate gastric and intestinal fluids corresponding to fasted and fed states. Osmolality, pH, viscosity, and other characteristics can be controlled to mimic physiological fluids. Dissolution tests can also be conducted using water.

One of skill will know how to conduct dissolution tests according to a number of known techniques. Dissolution tests are typically conducted at temperatures ranging from about 20° C. to 40° C., with or without mechanical agitation such as stirring. Dissolved and undissolved tozadenant can be quantified according to one or more known techniques including, but not limited to, UV-visible absorption spectroscopy, mass spectrometry, liquid chromatography (including high performance liquid chromatography (HPLC, and ultra performance liquid chromatography (UPLC)), gas chromatography, and weighing.

In some embodiments, the test procedure for assessing tozadenant dissolution during the test period includes stirring the composition with paddles at about 50-100 rpm in a volume of test solution containing 0.1 M hydrochloric acid and 1% (w/w) sodium dodecylsulfate. Typically, the test solution is used in volumes ranging from about 200 mL to about 1000 mL. In some embodiments, the ratio of the test solution to the total composition is about 1800/1 (w/w). One of skill in the art will appreciate that the ratio of the test solution to the total composition is typically a function of the tablet weight, and that the volume of test solution may not increase proportionately with tablet weight. Various types of sinker devices, to prevent floating of the sample, may or may not be used during the test. Instead of a paddle apparatus, other apparatuses may be used such as a basket apparatus, a reciprocating cylinder, or a flow-through cell. Other test procedures, as described, for example, in United States Pharmacopeia Chapter <711> and European Pharmacopeia Section 2.9.3, can be used to assess tozadenant dissolution during the test period.

Controlled release of tozadenant from a composition of the invention arises, in part, from swelling of the cellulose ether in aqueous environments which prevents dissolution and diffusion of the tozadenant from the composition. One of skill in the art will appreciate that other hydrophilic polymers can be used in the compositions of the invention including, but not limited to, alginic acid and salts thereof; guar gum; gum arabic; tragacanth; xanthan gum; agar; pectin and derivatives thereof; chitin and derivatives thereof; polyacrylic acids and salts thereof; polymethacrylic acids and salts thereof; methacrylate copolymers; polyvinylalcohol; polyvinylpyrrolidone and polyvinylpyrrolidone copolymers; polyalkylene oxides, such as polyethylene oxide and polypropylene oxide; and polyalkylene oxide copolymers.

Cellulose ethers are particularly useful in the compositions of the invention. As described above, cellulose ethers are polymeric carbohydrates having a backbone made up of β(1→4) linked D-glucose subunits. Cellulose ethers include, but are not limited to: alkylcelluloses such as methylcellulose; hydroxyalkylcelluloses such as hydroxymethylcellulose, hydroxyethylcellulose, hydroxypropylcellulose and hydroxybutylcellulose; hydroxyalkyl alkylcelluloses such as hydroxyethyl methylcellulose and hydroxypropyl methylcellulose; carboxyalkylcelluloses, such as carboxymethylcellulose, and salts thereof; carboxyalkylcellulose esters; and carboxyalkylalkylcelluloses, such as carboxymethylethylcellulose, and salts thereof.

A cellulose ether can be used in any amount suitable for achieving a particular tozadenant dissolution profile or for obtaining a targeted pharmacokinetic parameter. For example, the cellulose ether can be present in an amount sufficient to provide about 10-30% tozadenant dissolution over a 2-hour test period. The cellulose ether can be present in an amount sufficient to provide about 10-12%, or about 12-14%, or about 14-16%, or about 16-18%, or about 18-20%, or about 20-22%, or about 22-24%, or about 24-26%, or about 26-28%, or about 28-30% tozadenant dissolution over a 2-hour test period. The cellulose ether can be present in an amount sufficient to provide about 11-27%, or about 12-26%, or about 13-25%, or about 14-24%, or about 15-23%, or about 16-22%, or about 17-21%, or about 18-20% tozadenant dissolution over a 2-hour test period.

The cellulose ether can be present in an amount sufficient to provide about 11, 12, 13, 14, 15, 16, 17, 18, 19, 20, 21, 22, 23, 24, 25, 26, 27, 28, 29, or 30% tozadenant dissolution over a 2-hour test period. The cellulose ether can be present in an amount sufficient to provide not more than about 12, 13, 14, 15, 16, 17, 18, 19, 20, 21, 22, 23, 24, 25, 26, 27, 28, 29, or 30% tozadenant dissolution over a 2-hour test period. The cellulose ether can be present in an amount sufficient to provide not less than about 11, 12, 13, 14, 15, 16, 17, 18, 19, 20, 21, 22, 23, 24, 25, 26, 27, 28, or 29% tozadenant dissolution over a 2-hour test period.

Compositions of the invention can contain a cellulose ether in an amount sufficient to provide 30-80% tozadenant dissolution over a 6-hour test period. The cellulose ether can be present in an amount sufficient to provide about 30-34%, or about 34-39%, or about 39-44%, or about 44-49%, or about 49-54%, or about 54-59%, or about 59-64%, or about 64-69%, or about 69-74%, or about 74-77%, or about 77-80% tozadenant dissolution over a 6-hour test period. The cellulose ether can be present in an amount sufficient to provide about 32-77%, or about 35-72%, or about 38-68%, or about 41-65%, or about 44-62%, or about 47-59%, or about 50-56% tozadenant dissolution over a 6-hour test period.

The cellulose ether can be present in an amount sufficient to provide about 30, 32, 35, 38, 41, 44, 47, 50, 53, 56, 59, 62, 65, 68, 71, 74, 77, or 80% tozadenant dissolution over a 6-hour test period. The cellulose ether can be present in an amount sufficient to provide not more than about 32, 35, 38, 41, 44, 47, 50, 53, 56, 59, 62, 65, 68, 71, 74, 77, or 80% tozadenant dissolution over a 6-hour test period. The cellulose ether can be present in an amount sufficient to provide not less than about 29, 32, 35, 38, 41, 44, 47, 50, 53, 56, 59, 62, 65, 68, 71, 74, or 77% tozadenant dissolution over a 6-hour test period.

Compositions of the invention can contain a cellulose ether in an amount sufficient to provide 55-99% tozadenant dissolution over a 10-hour test period. The cellulose ether can be present in an amount sufficient to provide about 55-58%, or about 58-63%, or about 63-68%, or about 68-73%, or about 73-78%, or about 78-83%, or about 83-88%, or about 88-95% tozadenant dissolution over a 10-hour test period. The cellulose ether can be present in an amount sufficient to provide about 55-90%, or about 57-87%, or about 60-84%, or about 63-81%, or about 66-78%, or about 69-75%, or about tozadenant dissolution over a 10-hour test period.

The cellulose ether can be present in an amount sufficient to provide about 55, 57, 60, 63, 66, 69, 72, 75, 78, 81, 84, 87, 90, 93, 96, or 99% tozadenant dissolution over a 10-hour test period. The cellulose ether can be present in an amount sufficient to provide not more than about 57, 60, 63, 66, 69, 72, 75, 78, 81, 84, 87, 90, 93, 96, or 99% tozadenant dissolution over a 10-hour test period. The cellulose ether can be present in an amount sufficient to provide not less than about 55, 57, 60, 63, 66, 69, 72, 75, 78, 81, 84, 87, 90, 93, or 96% tozadenant dissolution over a 10-hour test period.

The cellulose ether can be present in an amount sufficient to provide not less than about 80% tozadenant dissolution over a 16-hour test period. The cellulose ether can be present in an amount sufficient to provide about 85-90%, about 90-95%, or greater than about 95% tozadenant dissolution over a 16-hour test period. The cellulose ether can be present in an amount sufficient to provide not less than about 85, 86, 87, 88, 90, 91, 92, 93, 94, 95, 96, 97, 98, 99, or 100% tozadenant dissolution over a 16-hour test period.

In some embodiments, the cellulose ether is present in an amount sufficient to provide not less than about 10% and not more than about 20% tozadenant dissolution over a 2-hour test period. In some embodiments, the cellulose ether is present in an amount sufficient to provide not less than about 35% and not more than about 55% tozadenant dissolution over a 6-hour test period. In some embodiments, the cellulose ether is present in an amount sufficient to provide not less than about 55% and not more than about 85% tozadenant dissolution over a 10-hour test period. In some embodiments, the cellulose ether is present in an amount sufficient to provide about 85% tozadenant dissolution over a 16-hour test period. In some embodiments, the cellulose ether is present in an amount sufficient to provide not less than about 90% tozadenant dissolution over a 16-hour test period.

In some embodiments, the cellulose ether is present in an amount sufficient to provide not less than about 20% and not more than about 30% tozadenant dissolution over a 2-hour test period. In some embodiments, the cellulose ether is present in an amount sufficient to provide not less than about 55% and not more than about 75% tozadenant dissolution over a 6-hour test period. In some embodiments, cellulose ether is present in an amount sufficient to provide not less than about 85% tozadenant dissolution over a 10-hour test period.

Any suitable mass of cellulose ether can be used in the compositions of the invention. In general, a cellulose ether (or mixture of cellulose ethers) will be present in an amount ranging from about 5% (w/w) to about 40% (w/w) based on the total weight of the composition. For example, the composition can contain about 5-10%, about 10-15%, about 15-20%, about 20-25%, about 25-30%, about 30-35%, or about 35-40% (w/w) cellulose ether. The composition can contain about 5-40%, about 8-37%, about 11-34%, about 14-31%, about 17-28%, or about 20-25% (w/w) cellulose ether. The composition can contain about 14, 15, 16, 17, 18, 19, 20, 21, 22, 23, 24, 25, 26, 27, or 28% (w/w) cellulose ether.

In some embodiments, the cellulose ether is present in an amount ranging from about 10% (w/w) to about 30% (w/w) based on the total composition weight.

In some embodiments, the cellulose ether is present in an amount ranging from about 22% (w/w) to about 28% (w/w) based on the total composition weight.

In some embodiments, the cellulose ether is present in an amount ranging from about 15% (w/w) to about 21% (w/w) based on the total composition weight.

In certain embodiments, compositions of the invention contain hydroxypropyl methylcellulose (HPMC). Typically, the HPMC is characterized by an apparent viscosity ranging from about 50 cP to about 150,000 cP (2% w/w in water at 20° C.). The apparent viscosity of the HPMC can vary, depending on factors including the degree of polymerization (i.e., the number of glucose subunits in the polymer backbone) and the degree of substitution (i.e., the number of methyl and hydroxypropyl groups in the glucose subunits). The apparent viscosity can be for example, from about 60 cP to about 140 cP, or from about 80 cP to about 120 cP (2% w/w in water at 20° C.). The apparent viscosity can be from about 2800 cP to about 5800 cP, or from about 3000 cP to about 5600 cP (2% w/w in water at 20° C.). HMPC characterized by other apparent viscosity values can be suitable for use in the compositions of the invention, depending on the targeted release profile.

Accordingly, some embodiments of the invention provide compositions containing tozadenant, at least one cellulose ether, and one or more pharmaceutically acceptable excipients as described above, wherein the cellulose ether comprises hydroxypropyl methylcellulose.

In some embodiments, the hydroxypropyl methylcellulose is characterized by an apparent viscosity ranging from about 60 cP to about 140 cP when formulated as a 2% (w/w) solution in water at 20° C. In some embodiments, the hydroxypropyl methylcellulose is characterized by an apparent viscosity ranging from about 2800 cP to about 5800 cP when formulated as a 2% (w/w) solution in water at 20° C.

In some embodiments, the cellulose ether is present in an amount ranging from about 22% (w/w) to about 28% (w/w) based on the total composition weight; the cellulose ether consists essentially of hydroxypropyl methylcellulose; and the hydroxypropyl methylcellulose is characterized by an apparent viscosity ranging from about 60 cP to about 140 cP when formulated as a 2% (w/w) solution in water at 20° C.

In some embodiments, the cellulose ether is present in an amount of about 25% (w/w) based on the total composition weight; the cellulose ether consists essentially of hydroxypropyl methylcellulose; and the hydroxypropyl methylcellulose is characterized by an apparent viscosity ranging from about 60 cP to about 140 cP when formulated as a 2% (w/w) solution in water at 20° C.

In some embodiments, the cellulose ether is present in an amount ranging from about 15% (w/w) to about 30% (w/w) based on the total composition weight; the cellulose ether consists essentially of hydroxypropyl methylcellulose; and the hydroxypropyl methylcellulose is characterized by an apparent viscosity ranging from about 2800 cP to about 5800 cP when formulated as a 2% (w/w) solution in water at 20° C.

In some embodiments, the cellulose ether is present in an amount ranging from about 15% (w/w) to about 21% (w/w) based on the total composition weight; the cellulose ether consists essentially of hydroxypropyl methylcellulose; and the hydroxypropyl methylcellulose is characterized by an apparent viscosity ranging from about 2800 cP to about 5800 cP when formulated as a 2% (w/w) solution in water at 20° C.

In some embodiments, the cellulose ether is present in an amount of about 18% (w/w) based on the total composition weight; the cellulose ether consists essentially of hydroxypropyl methylcellulose; and the hydroxypropyl methylcellulose is characterized by an apparent viscosity ranging from about 2800 cP to about 5800 cP when formulated as a 2% (w/w) solution in water at 20° C.

In some embodiments, the cellulose ether is present in an amount ranging from about 22% (w/w) to about 28% (w/w) based on the total composition weight; the cellulose ether consists essentially of hydroxypropyl methylcellulose; and the hydroxypropyl methylcellulose is characterized by an apparent viscosity ranging from about 2800 cP to about 5800 cP when formulated as a 2% (w/w) solution in water at 20° C.

In some embodiments, the cellulose ether is present in an amount of about 25% (w/w) based on the total composition weight; the cellulose ether consists essentially of hydroxypropyl methylcellulose; and the hydroxypropyl methylcellulose is characterized by an apparent viscosity ranging from about 2800 cP to about 5800 cP when formulated as a 2% (w/w) solution in water at 20° C.

Any suitable amount of tozadenant can be used in the compositions of the invention. In general, the compositions of the invention contain an amount of tozadenant sufficient to provide a $C_{max}$ of tozadenant below around 6 μg/mL when administered once a day for at least 14 days. In some embodiments, the compositions contain an amount of tozadenant sufficient to provide a $C_{max}$ of tozadenant below around 4.0 μg/mL when administered once a day for at least 14 days. Typical compositions contain from about 30% (w/w) to about 65% (w/w) tozadenant, based on the total weight of the composition. Tozadenant can be present in an amount of about 32-34%, about 34-36%, about 36-38%, about 38-40%, about 40-42%, 42-44%, about 44-46%, about 46-48%, about 48-50%, about 50-52%, about 52-54%, about 54-56%, about 56-58%, or about 58-60% (w/w). Tozadenant can be present in an amount of about 32-63%, about 40-60%, about 41-59%, about 42-58%, about 43-57%, about 44-56%, about 45-55%, about 46-54%, about 47-53%, about 48-52%, or about 49-51% (w/w). Tozadenant can be present in an amount of about 33, 36, 39, 42, 45, 46, 47, 48, 49, 50, 51, 52, 53, 54, or 55% (w/w).

In some embodiments, the tozadenant is present in an amount ranging from about 45% (w/w) to about 55% (w/w) based on the total composition weight. In some embodiments, the tozadenant is present in an amount of about 50% (w/w) based on the total composition weight.

Pharmaceutically acceptable salts of tozadenant can also be used in the compositions of the invention. Tozadenant salts can be prepared by combining tozadenant with at least a stoichiometric amount of a suitable acid. Suitable acids include hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Typically, compositions of present invention will contain one or more diluents as a carrier material. Suitable diluents include, either individually or in combination, substances such as lactose USP; lactose USP, anhydrous; lactose USP, spray dried; starch USP; directly compressible starch; mannitol USP; sorbitol; isomalt (6-O-α-D-glucopyranosyl-D-glucitol mixed with 1-O-α-D-glucopyranosyl-D-mannitol, e.g., GalenIQ™ 801); dextrose monohydrate; microcrystalline cellulose NF; dibasic calcium phosphate dihydrate NF; sucrose-based diluents; confectioner's sugar; monobasic calcium sulfate monohydrate; calcium sulfate dihydrate NF; calcium lactate trihydrate granular NF; dextrates NF (e.g., Emdex™); Celutab™; dextrose (e.g., Cerelose™); inositol; hydrolyzed cereal solids such as the Maltrons™ and Mor-Rex™; amylose; Rexcel™; powdered cellulose (e.g., Elcema™); calcium carbonate; glycine; bentonite; polyvinylpyrrolidone; and the like. Any suitable amount of diluent can be used in the compositions of the invention. For example, compositions of the invention can contain about 5-50%, 10-45%, 15-40%, 20-35%, or 25-30% diluent. Compositions of the invention can contain about 15-20% diluent or about 20-30% diluent. Compositions of the invention can contain about 15, 16, 17, 18, 19, 20, 21, 22, 23, 24, 25, 26, 27, 28, 29, or 30% diluent.

Additionally, compositions of the invention can include one or more lubricants. Suitable lubricants include, but are not limited to: metallic salts of fatty acids (such as aluminum stearate, calcium stearate, magnesium lauryl sulfate, magnesium stearate, sodium lauryl sulfate, sodium stearyl fumarate, zinc stearate, and the like); esters of fatty acids (such as glyceryl behenate, glyceryl behenate with polyethylene glycol behenate, glyceryl palmitostearate, glyceryl monostearate, glyceryl trimyristate, glyceryl tristearate, and the like); fatty acids and alcohols (such as palmitic acid, palmitoyl alcohol, stearic acid, stearyl alcohol, and the like); oils (such as hydrogenated castor oil hydrogenated, mineral oil, hydrogenated vegetable oil, and the like); and other substances such as fumaric acid, polyethylene glycol 4000, polyethylene glycol 6000, polytetrafluorethylene, and sodium benzoate. Any suitable amount of lubricant can be used in the compositions of the invention. For example, compositions of the invention can contain about 0.1-5% or about 0.1-3% lubricant. Compositions of the invention can contain about 0.25, 0.5, 0.75, 1, 1.25, 1.5, 1.75, 2, 2.25, 2.5, 2.75, 3, 3.25, 3.5, 3.75, 4, 4.25, 4.5, 4.75, or 5% lubricant.

The compositions of the invention can further include one or more substances for improving the handling of tozadenant during formulation. In certain instances, such substances can be used to obtain a desired tozadenant dissolution profile. Substances for improving the handling of tozadenant include, but are not limited to, anti-adherents and glidants such as calcium silicate, powdered cellulose, starch, talc, colloidal silicon dioxide, fumed silica (including hydrophilic fumed silica such as Aerosil® 200), magnesium oxide, and magnesium silicate. Any suitable amount of glidant or anti-adherent can be used in the compositions of the invention. For example, compositions of the invention can contain about 0.1-10% glidant or anti-adherent. Compositions of the invention can contain about 0.5-10%, 2-8.5%, 2-6%, 3.5-7%, or 4-6.5% glidant or anti-adherent. Compositions of the invention can contain about 1, 1.5, 2, 2.5, 3, 3.5, 4, 4.5, 5, 5.5, 6, 6.5, 7, or 7.5% glidant or anti-adherent.

Accordingly, some embodiments of the present invention provide a composition containing tozadenant, at least one cellulose ether, and one or more pharmaceutically acceptable excipients as described above, wherein the pharmaceutically acceptable excipients are selected from talc, silica, isomalt, and magnesium stearate.

Compositions of the invention can further include active agents used for treating conditions associated with the activity of the adenosine $A_{2A}$ receptor. Accordingly, compositions of the invention can contain additional agents for treating Alzheimer's disease; Parkinson's disease; Huntington's disease; schizophrenia; anxiety; pain; respiration deficits; depression; ADHD (attention deficit hyper-activity disorder); drug addiction to amphetamines, cocaine, opioids, ethanol, nicotine, or cannabinoids; asthma; allergic responses; hypoxia; ischemia; seizure; substance abuse; or other conditions associated with adenosine $A_{2A}$ receptor activity.

The compositions of the invention can contain tozadenant in combination with one or more anticonvulsants. Examples of anticonvulsants include, but are not limited to, acetazolamide, brivaracetam, carbamazepine, clonazepam, diazepam, divalproex, ethosuximide, ethotoin, felbamate, gabapentin, lamotrigine, levetiracetam, mephenytoin, mephobarbital, methsuximide, oxcarbazepin, paramethadione, phenacemide, pheneturide, phenobarbital, phenytoin, pregabalin, primidone, seletracetam, stiripentol, topiramate, trimethadione, valproicacid, vigabatrin, and zonisimide.

The compositions of the invention can contain tozadenant in combination with one or more analgesics. Examples of analgesics include, but are not limited to, acetaminophen, alfentanilhydrochloride, all opurinol, aspirin, auranofin, aurothioglucose, bromfenacsodium, buprenorphinehydrochloride, butorphanoltartrate, chochicine, codeine, codeinephosphate, codeinesulfate, dezocine, diclofenacsodiumdiflunisal, etodolac, fenoprofencalcium, fentanylcitrate, flurbiprofen, hydrocodonebitartrate, hydromorphonehydrochloride, ibuprofen, indomethacin, ketoprofen, levorphanoltartrate, meclofenamatesodium, mefenamicacid, meperidinehydrochloride, methadonehydrochloride, morphine, morphinesulfate, nabumetone, nalbuphinehydrochloride, naloxonehydrochloride, naltrexonehydrochloride, naproxen, naproxensodium, oxycodonehydrochloride, oxymorphonehydrochloride, oxyphenbutazone, pentazocine, phenylbutazone, piroxicam, propoxyphenehydrochloride, propoxyphenenapsylate, sufentanil, sulfinpyrazone, sulindac, tolmetinsodium, and tramadolhydrochloride.

The compositions of the invention can contain tozadenant in combination with one or more neuroprotective agents. A number of active agents in various classes are known to exhibit neuroprotective effects. The compositions of the invention can contain neuroprotective agents including, but not limited to, chlorpromazine, citalopram, dapoxetine, enecadin, escitalopram, flunarizine, fluoxetine, fluvoxamine, fosphenytoin, haloperidol, haloperidol, methotrimeprazine, metoclopramide, modafinil, nimodipine, olanzapine, paroxetine, prochlorperazine, propentofylline, riluzole, sertraline, and zimelidine.

In some embodiments, invention provides a composition containing tozadenant, at least one cellulose ether, and one or more pharmaceutically acceptable excipients as described above, wherein the composition further contains an active agent selected from levodopa, carbidopa, pramipexole, ropinerole, bromocriptine, entacapone, tocapone, amantadine, and combinations thereof.

In some embodiments, the composition comprises:
about 50% (w/w) tozadenant based on the total composition weight,
from about 2% (w/w) to about 6% (w/w) talc based on the total composition weight,
from about 0.5% (w/w) to about 1.5% (w/w) silica based on the total composition weight,
from about 16% (w/w) to about 21% (w/w) isomalt based on the total composition weight,
from about 0.25% (w/w) to about 2.5% (w/w) magnesium stearate based on the total composition weight, and
from about 15% (w/w) to about 30% (w/w) of the cellulose ether based on the total composition weight,
wherein the cellulose ether is characterized by an apparent viscosity ranging from about 2800 cP to about 5800 cP when formulated as a 2% (w/w) solution in water at 20° C.

In some embodiments, the composition comprises:
about 50% (w/w) tozadenant based on the total composition weight,
from about 2% (w/w) to about 6% (w/w) talc based on the total composition weight,
from about 0.5% (w/w) to about 1.5% (w/w) silica based on the total composition weight, from about 16% (w/w) to about 21% (w/w) isomalt based on the total composition weight, from about 0.25% (w/w) to about 2.5% (w/w) magnesium stearate based on the total composition weight, and from about 15% (w/w) to about 20% (w/w) of the cellulose ether based on the total composition weight, wherein the cellulose ether is characterized by an apparent viscosity ranging from about 2800 cP to about 5800 cP when formulated as a 2% (w/w) solution in water at 20° C.

In some embodiments, the composition comprises:

about 50% (w/w) tozadenant based on the total composition weight, from about 2% (w/w) to about 6% (w/w) talc based on the total composition weight, from about 0.5% (w/w) to about 1.5% (w/w) silica based on the total composition weight, from about 16% (w/w) to about 21% (w/w) isomalt based on the total composition weight, from about 0.25% (w/w) to about 2.5% (w/w) magnesium stearate based on the total composition weight, and from about 23% (w/w) to about 27% (w/w) of the cellulose ether based on the total composition weight, wherein the cellulose ether is characterized by an apparent viscosity ranging from about 60 cP to about 140 cP when formulated as a 2% (w/w) solution in water at 20° C.

IV. Administration of Tozadenant with Improved Pharmacokinetics

In a related aspect, the invention provides a composition containing tozadenant, at least one cellulose ether, and one or more pharmaceutically acceptable excipients. The tozadenant is present in the composition in an amount sufficient to, when the composition is administered orally once a day for at least 14 days, provide a tozadenant steady-state concentration ($C_{ss}$) that is equivalent to the $C_{ss}$ obtained from immediate-release formulations that are therapeutically effective when administered more than once-daily. The cellulose ether is present in the composition in an amount sufficient to provide a tozadenant maximum concentration ($C_{max}$) below a threshold that results in an unacceptable incidence or severity of adverse events when the composition is administered orally once a day for at least 14 days.

The $C_{ss}$ will vary depending, in part, on factors such as the particular composition that is administered and the particular subject. In general, however, the $C_{ss}$ obtained from once-daily administration of a composition of the invention is equivalent to the $C_{ss}$ obtained from administration of multiple doses (i.e., two or more doses per day) of an immediate-release formulation. The $C_{ss}$ can range, for example, from about 0.25 to about 5 µg/mL. The $C_{ss}$ can be about 0.25-4.75 µg/mL, or about 0.5-4.5 µg/mL, or about 0.75-4.25 µg/mL, or about 1.0-4.0 µg/mL, or about 1.25-3.75 µg/mL, or about 1.5-3.5 µg/mL, or about 1.75-3.25 µg/mL, or about 2.0-3.0 µg/mL, or about 2.25-2.75 µg/mL. The $C_{ss}$ can be about 0.25, 0.5, 0.75, 1.0, 1.25, 1.5, 1.75, 2.0, 2.25, 2.5, 2.75, 3.0, 3.25, 3.5, 3.75, 4.0, 4.25, 4.5, 4.75, or 5.0 µg/mL. In some embodiments, the $C_{ss}$ is in the range of about 1.0-4.0 µg/mL.

Similarly, $C_{max}$ will vary depending, in part, on factors such as the particular composition that is administered and the particular subject. In general, however, the $C_{max}$ will be below the threshold resulting in unacceptable incidence or severity of adverse events. The $C_{max}$ threshold can range, for example, from about 1.0 to about 7.5 µg/mL. The $C_{max}$ threshold can be about 1.25-7.25 µg/mL, or about 1.5-7.0 µg/mL, or about 1.75-6.75 µg/mL, or about 2.0-6.5 µg/mL, or about 2.25-6.25 µg/mL, or about 2.5-6.0 µg/mL, or about 2.75-5.75 µg/mL, or about 3.0-5.5 µg/mL, or about 3.25-5.25 µg/mL, or about 3.5-5.0 µg/mL, or about 3.75-4.75 µg/mL, or about 4.0-4.5 µg/mL. The $C_{max}$ threshold can be about 0.25, 0.5, 0.75, 1.0, 1.25, 1.5, 1.75, 2.0, 2.25, 2.5, 2.75, 3.0, 3.25, 3.5, 3.75, 4.0, 4.25, 4.5, 4.75, 5.0, 5.25, 5.5, 5.75, 6.0, 6.25, 6.5, 6.75, or 7 µg/mL. In some embodiments, the $C_{max}$ threshold is in the range of about 2.0-5.0 µg/mL.

In certain cases, the compositions and methods of the present invention can provide reduced tozadenant side effects as compared to tozadenant administered without a controlled-release profile. For example, the compositions of the invention can allow for the treatment of Parkinson's disease with fewer incidences of dyskinesia, dizziness, nausea, flushing or transient hypertension than reported for treatment of Parkinson's disease with known tozadenant formulations. Without wishing to be bound by any particular theory, it is believed that the reduction in side effects is due, at least in part, to the reduced tozadenant $C_{max}$ provided by the compositions of the invention.

V. Methods for Treating Parkinson's Disease

In another aspect, the invention provides a method for treating Parkinson's disease. The method includes administering a therapeutically effective amount of levodopa and a therapeutically effective amount of a tozadenant composition according to the invention to a patient in need thereof.

Any suitable dose of tozadenant can be used in the methods of the invention. In general, tozadenant is administered at doses ranging from about 50 mg/day to about 1000 mg/day. For example, the tozadenant dose can be about 50-100 mg/day, or about 100-150 mg/day, or about 150-200 mg/day, or about 200-250 mg/day, or about 250-300 mg/day, or about 300-350 mg day, or about 350-400 mg/day, or about 400-450 mg/day, or about 450-500 mg/day, or about 500-550 mg/day, or about 550-600 mg/day, or about 600-650 mg/day, or about 650-700 mg/day, or about 700-750 mg/day, or about 750-800 mg/day, or about 800-850 mg/day, or about 850-900 mg/day, or about 900-950 mg/day, or about 950-1000 mg/day. The tozadenant dose can be about 60-990, about 70-980, about 80-970, about 90-960, about 100-950, about 110-940, about 120-930, about 130-920, about 140-910, about 150-900, about 160-890, about 170-880, about 180-870, about 190-860, about 200-850, about 210-840, about 220-830, about 230-820, about 240-810, about 250-800, about 260-790, about 270-780, about 280-770, about 290-760, about 300-750, about 310-740, about 320-730, about 330-720, about 340-710, about 350-700, about 360-690, about 370-680, about 380-670, about 390-660, about 400-650, about 410-640, about 420-630, about 430-620, about 440-610, about 450-600, about 460-590, about 470-580, about 480-570, about 490-560, or about 500-550 mg/day. The tozadenant dose can be about 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500 mg/day. In some embodiments, the tozadenant dose is about 240 mg/day. In some embodiments, the tozadenant does is about 360 mg/day. Preferably, the tozadenant is administered not more than twice per day. The composition contains sufficient tozadenant to be therapeutically effective with once-daily dosing. Preferably, the tozadenant is administered once per day as a single dose. The single dose can consist of a single controlled-release tablet, or the single dose can contain more than one controlled-release tablet. For example, the single dose can contain two controlled-release tablets or three controlled-release tablets. In certain embodiments, a tozadenant composition of the invention is administered in an amount sufficient to reduce levodopa off-time.

Any suitable dose of levodopa can be used in the methods of the invention. In general, levodopa is administered as doses ranging from about 250 mg/day to about 2000 mg/day. The total daily dose of levodopa is typically administered in three or more divided doses.

The dosage of tozadenant and/or levodopa can be varied depending upon the requirements of the patient, the severity of the Parkinson's disease, and the particular formulation being administered. The size of the dose will also be determined by the existence, nature, and extent of any adverse side-effects that accompany the administration of the drug in a particular patient. Determination of the proper dosage for a particular situation is within the skill of the typical practitioner.

One of skill in the art will appreciate that other conditions can be treated using the controlled-release compositions of the invention. Such diseases include, but are not limited to, Alzheimer's disease, Huntington's disease, schizophrenia, anxiety, pain, respiration deficits, depression, ADHD (attention deficit hyper-activity disorder), drug addiction to amphetamines, cocaine, opioids, ethanol, nicotine, or cannabinoids. The compositions can also be used for the treatment of asthma, allergic responses, hypoxia, ischemia, seizure, substance abuse, and cancer. In addition, the compositions of the invention can be used as muscle relaxants, neuroprotectants, antipsychotics, antiepileptics, anticonvulsants, and cardioprotective agents.

VI. Examples

Example 1. Tozadenant Characterization

The physical characteristics of tozadenant were studied as summarized in Table 1. The active pharmaceutical ingredient (API) was very fine, with ~60% fines. The API showed very low bulk and tapped density, and very poor flow character. The observed loss upon drying indicated a low amount of water and volatile matter in API.

TABLE 1

| Physical characterization of tozadenant API Visual Observation | |
|---|---|
| Observation | White to off-white fine loose powder |
| Particle size distribution (% Retention) | |
| ASTM # 20 mesh (841µ) | 0.00 |
| ASTM # 40 mesh (420µ) | 7.00 |
| ASTM # 60 mesh (250µ) | 33.00 |
| ASTM # 80 mesh (177µ) | 18.00 |
| ASTM # 100 mesh (149µ) | 16.00 |
| ASTM # 200 mesh (75µ) | 21.00 |
| Pan | 5.00 |
| Granular Portion (# 60 Retain portion) | 40.00 |
| Fines Portion (# 60 pass portion) | 60.00 |
| Bulk density and Tapped density (BD/TD) | |
| Bulk density (g/ml) | 0.1948 |
| Tapped density (g/ml) | 0.3000 |

TABLE 1-continued

| Physical characterization of tozadenant API Visual Observation | |
|---|---|
| Observation | White to off-white fine loose powder |
| Compressibility index | 35.065 |
| Hausner ratio | 1.5406 |
| Loss on drying at 105° C. for 5 minutes | |
| % w/w | 0.400 |

Figure 1:
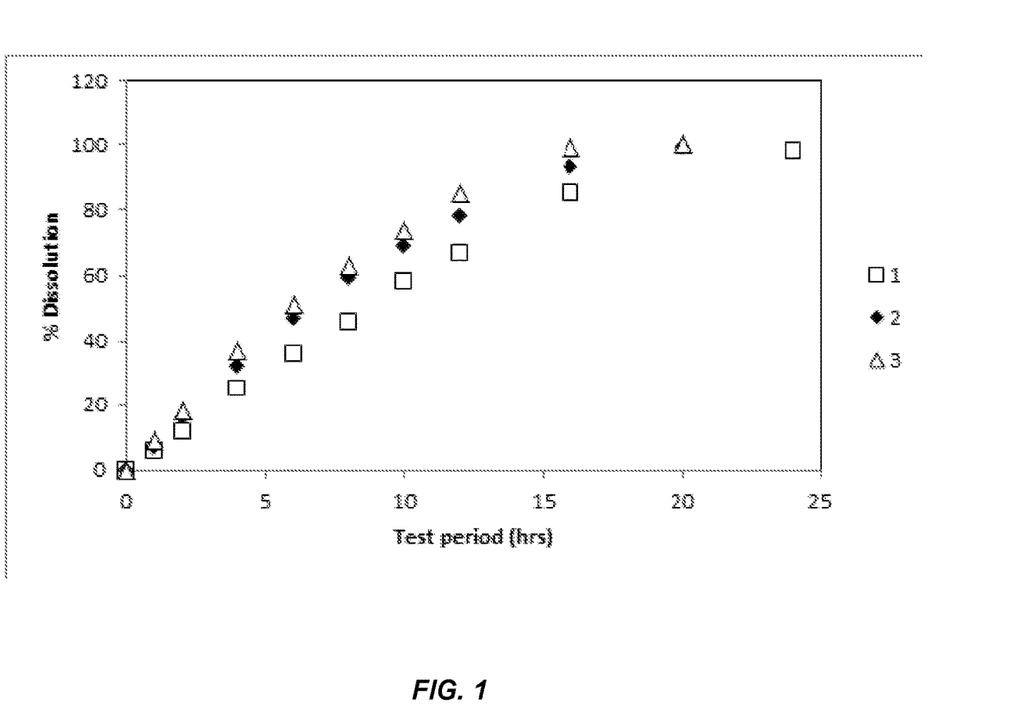
FIG. 1 shows dissolution of tozadenant formulations of the invention over time.

Example 2. SYN115 Controlled-Release (CR) Tablets 240 mg with Dissolution Profile of about 90% in 16 hrs New tablet dosage forms containing a 240-mg tozadenant dose with 50-60% (w/w) drug loading in a matrix containing cellulose ether were developed. The API was fine, cohesive and static, so wet granulation was used for compounding. 50% (w/w) drug loading was used to investigate methods of handling the fine and cohesive API. Incorporation of talc and aerosil in the formulations decreased handling difficulties. Initial formulations exhibited dissolution below the target levels. Judicious use of cellulose ether and isomalt provided the formulations exhibiting not less than about 90% dissolution at 16 hours under the test conditions (0.1M HCL+1% SDS, 100 rpm, paddle, 900 mL, no sinker; n=6). See, e.g., Formulation 3 in Table 2. As shown in FIG. 1 and Table 4, a small decrease in the polymer concentration from 20% to 18% significantly increased the drug release by 16 hrs in dissolution medium. Advantageously, Formulation 3 provided significant improvements in material handling and reduced losses of tozadenant.

TABLE 2

| Tozadenant compositions. | | | | | | |
|---|---|---|---|---|---|---|
| | 1 | | 2 | | 3 | |
| | Batch size | | | | | |
| | 200 g | | 100 g | | 192 g | |
| Ingredients | mg/tablet | % w/w | mg/tablet | % w/w | mg/tablet | % w/w |
| SYN115 | 240 | 60 | 240 | 50 | 240 | 50 |
| Talc | 0 | 0 | 4.8 | 1 | 19.2 | 4 |
| Aerosil 200 | 0 | 0 | 1 | 0.21 | 4.8 | 1 |
| Isomalt 801 (Galen IQ) | 52.8 | 13.2 | 131 | 27.29 | 122.4 | 25.5 |
| Methocel K4 M premium CR | 100 | 25 | 96 | 20 | 86.4 | 18 |
| Magnesium stearate | 7.2 | 1.8 | 7.2 | 1.5 | 7.2 | 1.5 |
| Total | 400 | 100 | 480 | 100 | 480 | 100 |

TABLE 3

| Dissolution of tozadenant compositions* | | | |
|---|---|---|---|
| | 1 | 2 | 3 |
| Time in hrs | | % Release | |
| 0 | 0 | 0 | 0 |
| 1 | 6 | 7 | 9 |
| 2 | 12 | 16 | 18 |
| 4 | 25 | 32 | 37 |

TABLE 3-continued

Dissolution of tozadenant compositions*

| Time in hrs | 1 | 2 | 3 |
|---|---|---|---|
| | | % Release | |
| 6 | 36 | 47 | 51 |
| 8 | 46 | 59 | 63 |
| 10 | 58 | 69 | 74 |
| 12 | 67 | 78 | 85 |
| 16 | 85 | 93 | 99 |
| 20 | NT | 99 | 100 |
| 24 | 98 | NT | NT |

*0.1M HCl + 1% SDS, 100 rpm, paddle, 900 mL, no sinker (n = 6).
NT = not tested.

TABLE 4

Comparison of tozadenant compositions

| | 1 | 2 | 3 |
|---|---|---|---|
| Tozadenant dose (mg) | 240 | 240 | 240 |
| Tozadenant content (% w/w) | 60 | 50 | 50 |
| Cellulose ether content (% w/w) | 25 | 20 | 18 |
| Tozadenant dissolution at 16 hr (%) | 85 | 93 | 99 |
| Gain in tozadenant dissolution* | n/a | +9.4% | +16.5% |

*relative gain compared to composition 1

Example 3. Stability and Scale-Up of Tozadenant Formulation

Formulation 3 from Example 2 was stored at elevated temperature and humidity, as summarized in Table 5. The formulation was stable over the study period. No change in drug content, impurity levels, and dissolution profile were observed after storage at 40° C./75% RH for 1 month or 3 months.

TABLE 5

Stability data for tozadenant formulation 3

| Stability Condition | Initial | 1 Month (40° C./ 75% RH) | 3 Month (40° C./75% RH) |
|---|---|---|---|
| % Assay | 100.6 | 100.3 | 101.3 |
| % Water Content | 2.22 | 1.31 | 1.45 |
| % Impurity/Degradation products | | | |
| RRT | | | |
| 0.66 | BQL | BQL | BQL |
| 0.76 | BQL | 0.058 | BQL |
| 0.91 | BQL | BQL | 0.036 |
| 1.22 | BQL | ND | ND |
| Total Impurities (%) | NA | 0.058 | 0.036 |
| Run Specific LOQ (%) | 0.026 | 0.029 | 0.030 |
| Time points (hrs) | % Cumulative drug release | | |
| Dissolution: 1 | 9 | 8 | 8 |
| 0.1N HCl + 2 | 18 | 18 | 17 |
| 1% SDS* 4 | 37 | 36 | 35 |
| 6 | 51 | 51 | 51 |

TABLE 5-continued

Stability data for tozadenant formulation 3

| Stability Condition | Initial | 1 Month (40° C./ 75% RH) | 3 Month (40° C./75% RH) |
|---|---|---|---|
| 8 | 63 | 64 | 64 |
| 10 | 74 | 74 | 74 |
| 12 | 85 | 82 | 83 |
| 16 | 99 | 96 | 96 |
| 20 | 100 | 101 | 101 |

BQL = Below Quantitation Limit (below LOQ);
ND = Not Detected
*100 rpm, paddle, 900 mL, no sinker (n = 6)

Figure 3:
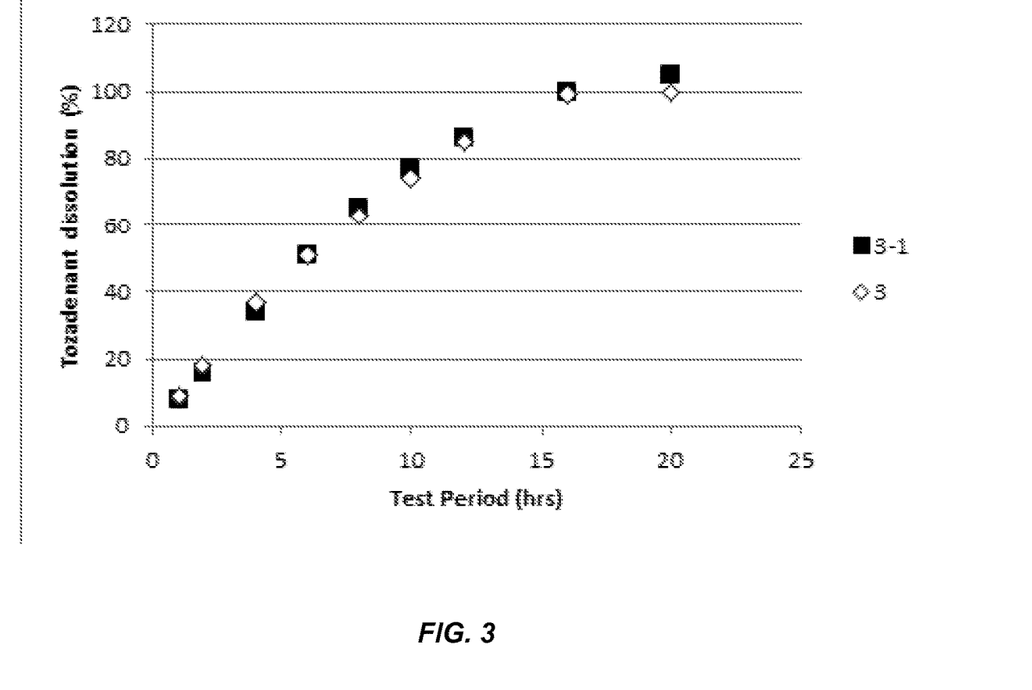
FIG. 3 shows dissolution over time of tozadenant formulations of the invention prepared on different scales.

The formula and process used for preparation of Formulation 3 in Table 3 was used for manufacture of an initial scale-up batch at a batch size of 480 g. See, Formulation 3-1, Table 6. The initial scale-up batch 3-1 for SYN115 CR tablets 240 mg (NLT 90% in 16 hrs) showed results similar to the final feasibility batch (Formulation 3). See, FIG. 3.

TABLE 6

Scale-up Formulation 3-1.
Formulation 3-1

| | Batch size 480 g | |
|---|---|---|
| Ingredients | mg/tablet | % w/w |
| SYN115 | 240.00 | 50.00 |
| Talc | 19.20 | 4.00 |
| Aerosil 200 | 4.80 | 1.00 |
| Isomalt 801 (Galen IQ) | 122.40 | 25.50 |
| Methocel K4 M premium CR | 86.40 | 18.00 |
| Magnesium stearate | 7.20 | 1.50 |
| Avg. wt. | 480.00 | 100.00 |

TABLE 7

Dissolution data for scale-up Formulation 3-1.
Dissolution: 0.1M HCL + 1% SDS, 100 rpm,
paddle, 900 ml, no sinker, n = 6

| Time in hrs | % Released |
|---|---|
| 1 | 8 |
| 2 | 16 |
| 4 | 34 |
| 6 | 51 |
| 8 | 65 |
| 10 | 77 |
| 12 | 86 |
| 16 | 100 |
| 20 | 105 |

Figure 2:
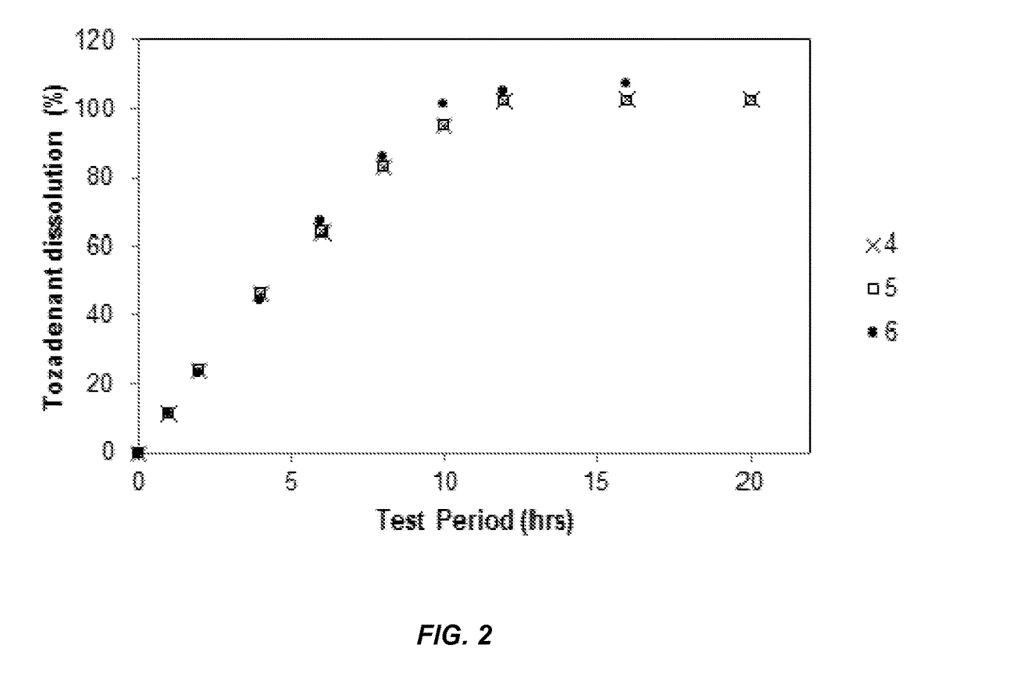
FIG. 2 shows dissolution of tozadenant formulations of the invention over time.

Example 4. SYN115 CR Tablets 240 mg with Dissolution Profile of about 90% in 10 hrs A low viscosity grade polymer, Methocel K100 premium LVCR, provided dissolution of tozadenant with about 90% drug release in 10 hrs when used at 25% (w/w). See, e.g., Formulation 4 in Table 8. Use of talc and aerosil to improve handling did not negatively affect the dissolution profile of the SYN115. Surprisingly, in fact, increasing the concentration of talc and aerosil improved the dissolution profile and the dissolution value at 10 hr for Formulation 6. See, e.g., Formulations 5 and 6 in Table 10 and FIG. 2.

TABLE 8

Tozadenant compositions.

| | 4 | | 5 | | 6 | |
|---|---|---|---|---|---|---|
| | Batch size | | | | | |
| | 100 g | | 192 g | | 50 g | |
| Ingredients | mg/tablet | % w/w | mg/tablet | % w/w | mg/tablet | % w/w |
| SYN115 | 240.00 | 50.00 | 240.00 | 50.00 | 240.00 | 50.00 |
| Talc | 4.80 | 1.00 | 7.20 | 1.50 | 19.20 | 4.00 |
| Aerosil 200 | 1.00 | 0.21 | 2.40 | 0.50 | 4.80 | 1.00 |
| Isomalt 801 (Galen IQ) | 107.00 | 22.29 | 103.20 | 21.50 | 88.80 | 18.50 |
| Methocel K100 premium LVCR | 120.00 | 25.00 | 120.00 | 25.00 | 120.00 | 25.00 |
| Magnesium stearate | 7.20 | 1.50 | 7.20 | 1.50 | 7.20 | 1.50 |
| Total | 480.00 | 100.00 | 480.00 | 100.00 | 480.00 | 100.00 |

TABLE 9

Dissolution of tozadenant compositions*

| | 4 | 5 | 6 |
|---|---|---|---|
| Time in hrs | | % Release | |
| 0 | 0 | 0 | 0 |
| 1 | 11 | 11 | 11 |
| 2 | 24 | 24 | 23 |
| 4 | 46 | 46 | 44 |
| 6 | 64 | 64 | 67 |
| 8 | 83 | 83 | 86 |
| 10 | 95 | 95 | 101 |
| 12 | 102 | 102 | 105 |
| 16 | 103 | 102 | 107 |
| 20 | 103 | 102 | NT |

*0.1M HCL + 1% SDS, 100 rpm, paddle, 900 mL, no sinker (n = 6).
NT = not tested.

TABLE 10

Comparison of tozadenant compositions

| | 4 | 5 | 6 |
|---|---|---|---|
| Tozadenant dose (mg) | 240 | 240 | 240 |
| Tozadenant content (% w/w) | 50 | 50 | 50 |
| Cellulose ether content (% w/w) | 25 | 25 | 25 |
| Talc content (% w/w) | 1.00 | 1.50 | 4 |
| Aerosil content (% w/w) | 0.21 | 0.50 | 1 |
| Tozadenant dissolution at 10 hr (%) | 95 | 95 | 101 |
| Gain in tozadenant dissolution* | n/a | 0% | 6.3% |

*relative gain compared to composition 4

Example 5. Stability and Scale-Up of Tozadenant Formulation

Formulation 5 from Example 4 was stored at elevated temperature and humidity, as summarized in Table 11. The formulation was stable over the study period. No change in drug content, impurity levels, and dissolution profile were observed after storage at 40° C./75% RH for 1 month or 3 months.

TABLE 11

Stability data for tozadenant formulation 5

| Stability Condition | Initial | 1 Month (40° C./75% RH) | 3 Month (40° C./75% RH) |
|---|---|---|---|
| % Assay | 97.3 | 99.5 | 98.9 |
| % Water Content | 2.89 | 2.23 | 2.10 |
| % Impurity/Degradation products | | | |
| RRT | | | |
| 0.66 | BQL | BQL | BQL |
| 0.76 | BQL | ND | BQL |
| 0.91 | BQL | ND | BQL |
| 1.22 | BQL | ND | BQL |
| Total Impurities (%) | NA | NA | NA |
| Run Specific LOQ (%) | 0.030 | 0.028 | 0.030 |

| Time points (hrs) | % Cumulative drug release | | |
|---|---|---|---|
| Dissolution: 0.1N HCl + 1% SDS* | | | |
| 1 | 11 | 11 | 11 |
| 2 | 24 | 23 | 24 |
| 4 | 46 | 48 | 49 |
| 6 | 64 | 68 | 69 |
| 8 | 83 | 84 | 84 |
| 10 | 95 | 94 | 94 |
| 12 | 102 | 99 | 98 |
| 16 | 102 | 101 | 99 |
| 20 | 102 | 101 | 99 |

*100 rpm, paddle, 900 mL, no sinker (n = 6)

Figure 4:
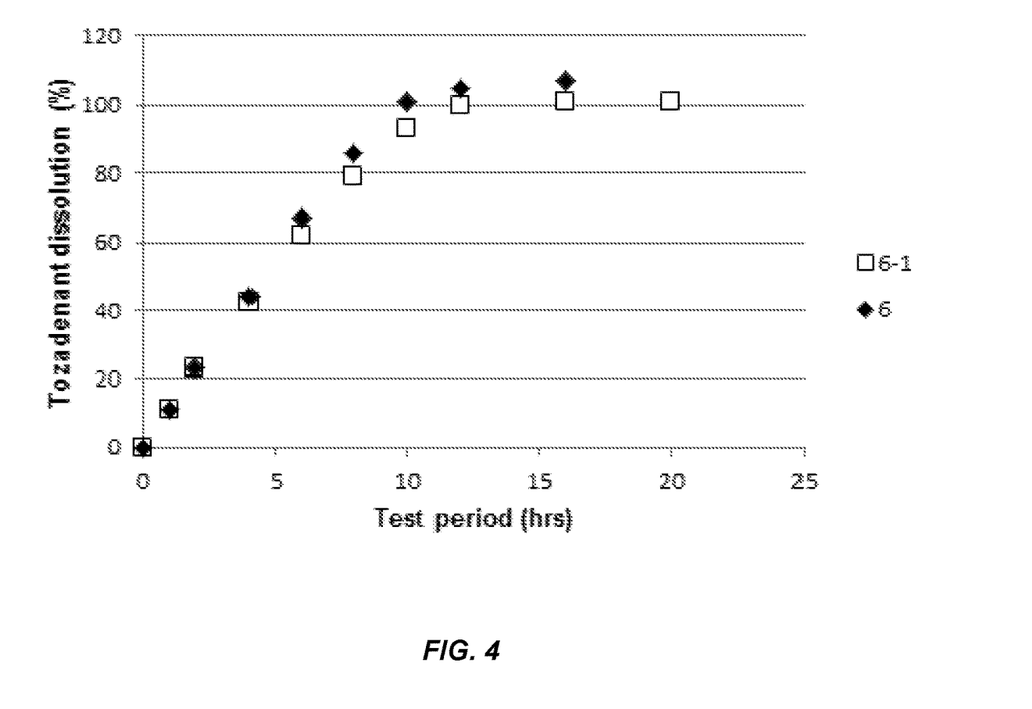
FIG. 4 shows dissolution over time of tozadenant formulations of the invention prepared on different scales.

The formula and process used for Formulation 6 was used to prepare a final scale-up batch 6-1 at a batch size of 192 g. The scale up Formulation 6-1 for SYN115 CR tablets 240 mg (NLT about 90% in 10 hrs) showed results similar to Formulation 6. See, e.g., FIG. 4. No significant change in assay, impurities and dissolution profile was observed for the scale-up batch during stability at 40° C./75% RH conditions for 1 and 3 months.

TABLE 12

Scale-up Formulation 6-1.
Formulation 6-1

| | Batch size 192 g | |
|---|---|---|
| Ingredients | mg/tablet | % w/w |
| SYN115 | 240.00 | 50.00 |
| Talc | 19.20 | 4.00 |
| Aerosil 200 | 4.80 | 1.00 |
| Isomalt 801 (Galen IQ) | 88.80 | 18.50 |
| Methocel K100 premium LVCR | 120.00 | 25.00 |
| Magnesium stearate | 7.20 | 1.50 |
| Total | 480.00 | 100.00 |

TABLE 13

Dissolution data for scale-up Formulation 6-1.
Dissolution: 0.1M HCL + 1% SDS, 100 rpm, paddle, 900 ml, no sinker N = 6

| Time in hrs | % Released |
|---|---|
| 0 | 0 |
| 1 | 11 |

TABLE 13-continued

Dissolution data for scale-up Formulation 6-1.
Dissolution: 0.1M HCL + 1% SDS, 100 rpm,
paddle, 900 ml, no sinker N = 6

| Time in hrs | % Released |
|---|---|
| 2 | 23 |
| 4 | 42 |
| 6 | 62 |
| 8 | 79 |
| 10 | 93 |
| 12 | 100 |
| 16 | 101 |
| 20 | 101 |

Example 6. SYN115 CR Tablets 240 mg (NLT 90% in 16 hrs)—Final Scale Up

Formulations described above were developed to achieve dissolution of at least about 90% in 10 hrs and at least about 90% in 16 hours. The strategies developed were able to achieve the target dissolution specifications. The difference in time to achieve exactly 90% dissolution level between two dissolution profiles was around 3.63 hrs, as calculated via model fitting for T90% calculation.

In certain instances, having a difference of at least about 6 hrs to achieve the 90% dissolution level between two dissolution profiles is desirable. Accordingly, a final scale-up batch containing 25% (w/w) cellulose for the SYN115 CR Tablets 240 mg NLT 90% in 16 hrs was manufactured at a batch size of 300 g. See, Table 14.

TABLE 14

Composition and Results for Final Scale-up Batch
for SYN115 CR tablets 240 mg (NLT 90% in 16 hrs)

| | Batch size 300 g | |
|---|---|---|
| Ingredients | mg/tablet | % w/w |
| SYN115 | 240.00 | 50.00 |
| Talc | 19.20 | 4.00 |
| Aerosil 200 | 4.80 | 1.00 |
| Isomalt 801 (Galen IQ) | 88.80 | 18.50 |
| Methocel K4M premium CR | 120.00 | 25.00 |
| Magnesium stearate | 7.20 | 1.50 |
| Total | 480.00 | 100.00 |

TABLE 15

Dissolution data for for Final Scale-up Batch for
SYN115 CR tablets 240 mg (NLT 90% in 16 hrs).
Dissolution: 0.1M HCL + 1% SDS, 100 rpm, paddle, no sinker
N = 6

| Time in hrs | % Released |
|---|---|
| 0 | 0 |
| 1 | 5 |
| 2 | 12 |
| 4 | 23 |
| 6 | 34 |
| 8 | 46 |
| 10 | 57 |
| 12 | 68 |
| 16 | 85 |
| 20 | 96 |
| 24 | 99 |

Example 7. Pilot-Scale Manufacturing

API and excipients were dispensed in the amounts required for the manufacture of the pilot batches as shown in Table 16 and Table 17. SYN115, Talc and Aerosil 200 were sifted through ASTM #20 sieves; and Galen IQ801 and cellulose ether were sifted through ASTM #40. The sifted materials were dry-mixed in a 5 liter rapid mixer granulator bowl at slow speed for 10 minutes. 500 gm of purified water was accurately weighed and used to granulate the dry-mixed material. Additional water was added as necessary. The resulting wet granules were dried using a fluid bed dryer for 10 minutes at 55° to 60° C. The resulting semidried granules were milled through a 3.96 mm sieve using Quadrocomil. The resulting milled granules were dried further using a fluid bed dryer at 55° to 60° C. until loss on drying was not more than 2% w/w. The dried granules were sized through an ASTM #20 sieve, and the oversized granules retained on the sieve were collected. The oversized granules were milled through a 1.00 mm screen using Quadrocomil. The granules passed through ASTM #20 sieve were combined with the granules milled through the 1.00 mm screen were lubricated with magnesium stearate in a 6 L Conta blender bin at 20 rpm for 5 minutes. Prior to lubrication, the magnesium stearate was weighed and sifted through an ASTM #60 sieve. The resulting lubricated blend was compressed using 15.45*6.32 mm tablet shaped punches to target tablet core weight of 480 mg. The core tablets were not film-coated or further processed.

TABLE 16

Composition of SYN115 CR Tablets 240 mg
(NLT 90% in 16 hrs) Pilot Batch

| Ingredient | mg/tablet | % w/w | g/batch |
|---|---|---|---|
| SYN115 | 240.00 | 50.00 | 725.8 |
| Talc | 19.20 | 4.00 | 57.6 |
| Aerosil 200 | 4.80 | 1.00 | 14.4 |
| Galen IQ 801 | 88.80 | 18.50 | 260.6 |
| Methocel K4M premium CR | 120.00 | 25.00 | 360.0 |
| Magnesium stearate | 7.20 | 1.50 | 21.6 |
| Total | 480.00 | 100.00 | 1400.0 |

The dissolution using sinkers was ~5% faster in comparison to dissolution without sinkers. This is because the use of sinkers prevented the tablet, or pieces of tablet, from sticking to the bottom of the vessel or floating to the top, hence improving the surface area contact with dissolution media, resulting in somewhat faster and more complete dissolution.

TABLE 17

Composition of SYN115 CR Tablets 240 mg
(NLT 90% in 10 hrs), Pilot batch.

| Ingredient | mg/tablet | % w/w | g/batch |
|---|---|---|---|
| SYN115 | 240.00 | 50.00 | 725.8 |
| Talc | 19.20 | 4.00 | 57.6 |
| Aerosil 200 | 4.80 | 1.00 | 14.4 |
| Galen IQ 801 | 88.80 | 18.50 | 260.6 |
| Methocel K 100 premium LVCR | 120.00 | 25.00 | 360.0 |
| Magnesium stearate | 7.20 | 1.50 | 21.6 |
| Total | 480.00 | 100.00 | 1400.0 |

Example 8. Clinical Study of Immediate-Release Tozadenant Compositions

Advantages of controlled-release formulations compared to immediate-release formulations include: lower incidence of adverse events; improved tolerability; reduced frequency of dosing; and improved compliance due to reduced frequency of dosing. The data set forth in Table 18 (including total Adverse Events (AE) per subject, $C_{max}$, and $C_{ss}$ shows a clear difference in the number of AEs per subject produced (0.7 vs. 2.7) between 120 mg twice-a-day (BID; total daily dose of 240 mg) and 240 mg once-a-day (QD). Further, the data in Table 19 shows a relationship between AEs and tozadenant plasma $C_{max}$ with an immediate-release formulation.

Table 18 also shows a trend toward increasingly higher AEs per subject (4.0 and 5.0) for the subjects that received 480 mg/day (either 240 mg BID or 480 mg QD), further indicating that a lower $C_{max}$ can reduce AEs. The groups receiving 480 mg/day (BID and QD) showed more AEs per subject as compared to the placebo and the 240 mg/day groups, and both of 480 mg/day groups showed a statistically significant higher $C_{max}$ as compared to the 240 mg/day groups.

AEs. An efficacious CR formulation would preferably result in a $C_{ss}$ in the range of 0.5-3.0 µg/mL.

TABLE 18

Summary of Treatment-Emergent Adverse Events (Safety Analysis Population).

| Type of Event | Placebo (N = 8) | SYN115 120 BID (N = 6) | SYN115 240 QD (N = 6) | SYN115 240 BID (N = 6) | SYN115 480 QD (N = 6) |
|---|---|---|---|---|---|
| Total Number of AEs | 18 | 4 | 16 | 24 | 30 |
| Total AEs/subject | 2.3 | 0.7 | 2.7 | 4.0 | 5.0 |
| $C_{max}$ (ng/mL) at Day 14 | — | 2971 | 3441 | 6157 | 5120 |
| Css (ng/mL) at Day 14 | — | 2364 | 2078 | 4806 | 3504 |

BID: Twice-a-day administration of immediate-release formulation of tozadenant
QD: Once-a-day administration of immediate-release formulation of tozadenant Table 19 summarizes the dose response of AEs observed in patients taking tozadenant alongside the plasma $C_{max}$. A clear trend of increasing AEs and discontinuation of therapy is seen with doses that result in higher tozadenant $C_{max}$. A controlled-release formulation can be used to achieve the drug levels ($C_{ss}$) that are therapeutically effective while avoiding the high plasma $C_{max}$ and AEs associated with high doses of an IR formulation.

TABLE 19

Summary of Treatment-Emergent Adverse Events and Tozadenant Plasma Cmax by Dose

| | Placebo (N = 84) | 60 mg BID (N = 85) | 120 mg BID (N = 82) | 180 mg BID (N = 85) | 240 mg BID (N = 84) |
|---|---|---|---|---|---|
| Patients with ≥ 1 AE related to study drug, % | 32 | 44 | 55 | 55 | 63 |
| Patients discontinuing due to AEs, % | 4 | 8 | 12 | 12 | 20 |
| Patients with no AE, % | 35 | 28 | 26 | 21 | 18 |
| $C_{max}$ (ng/mL) at ~5 hr postdose at Day 1 | — | 424 | 680 | 999 | 1148 |
| $C_{max}$ (ng/mL) at Week 6* | — | 2570 | 3910 | 5460 | 6630 |

*Maximum plasma concentration measured from a group ranging in size from 63-75 patients, the time between the most recent doses and obtaining the samples are unknown No statistical overlap between $C_{max}$ and $C_{ss}$ was observed during the 240 mg QD group, indicating that CR tablets can be used to obtain the $C_{ss}$ in a gradual fashion without the drug plasma spikes that may lead to AEs. The data shows that maintaining a lower $C_{max}$ can result in a lower incidence of AEs and improved tolerability. An example of an efficacious dose of tozadenant is 120 mg of an immediate-release formulation administered twice a day (BID). As shown in Table 18, the $C_{ss}$ for this regimen is about 2.4 µg/mL. Thus, a CR formulation could be designed to achieve an efficacious $C_{ss}$ lower than the plasma levels ($C_{max}$) that result in Of particular interest is the potential adverse effect of an increase in blood pressure (transient hypertension) after administration of immediate-release tozadenant. Increases in blood pressure have been observed in animals and human subjects upon administration of immediate-release tozadenant formulations. Controlled-released formulations can be used to achieve drug levels ($C_{ss}$) that are therapeutically effective, while avoiding the high plasma concentrations ($C_{max}$) that can contribute to the transient hypertension associated with high doses of immediate-release formulations.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A composition comprising tozadenant, at least one cellulose ether, and one or more pharmaceutically acceptable excipients,
wherein the tozadenant is present in an amount ranging from about 30% (w/w) to about 65% (w/w) based on the total composition weight,
wherein the cellulose ether is present in an amount sufficient to provide:
not less than about 10% and not more than about 30% tozadenant dissolution over a 2-hour test period,
not less than about 55% tozadenant dissolution over a 10-hour test period, and
not less than about 80% tozadenant dissolution over a 16-hour test period;
wherein the cellulose ether is present in an amount ranging from about 10% (w/w) to about 30% (w/w) based on the total composition weight; and
wherein the one or more pharmaceutically acceptable excipients comprise a glidant or anti-adherent in an amount ranging from about 0.5% to 10% based on the total composition weight.

2. The composition of claim 1, wherein the composition is stirred with paddles at 100 rpm in a test solution containing 0.1 M hydrochloric acid and 1% (w/w) sodium dodecylsulfate during the test period.

3. The composition of claim 1, wherein the cellulose ether is present in an amount sufficient to provide not less than about 10% and not more than about 20% tozadenant dissolution over a 2-hour test period.

4. The composition of claim 1, wherein the cellulose ether is present in an amount sufficient to provide not less than about 35% and not more than about 55% tozadenant dissolution over a 6-hour test period.

5. The composition of claim 1, wherein the cellulose ether is present in an amount sufficient to provide not less than about 55% and not more than about 85% tozadenant dissolution over a 10-hour test period.

6. The composition of claim 1, wherein the cellulose ether is present in an amount sufficient to provide not less than about 85% tozadenant dissolution over a 16-hour test period.

7. The composition of claim 1, wherein the cellulose ether is present in an amount sufficient to provide not less than about 90% tozadenant dissolution over a 16-hour test period.

8. The composition of claim 1, wherein the cellulose ether is present in an amount sufficient to provide not less than about 20% and not more than about 30% tozadenant dissolution over a 2-hour test period.

9. The composition of claim 1, wherein the cellulose ether is present in an amount sufficient to provide not less than about 55% and not more than about 80% tozadenant dissolution over a 6-hour test period.

10. The composition of claim 1, wherein the cellulose ether is present in an amount sufficient to provide not less than about 85% tozadenant dissolution over a 10-hour test period.

11. The composition of claim 1, wherein the cellulose ether is present in an amount sufficient to provide not less than about 90% tozadenant dissolution over a 10-hour test period.

12. The composition of claim 1, wherein the one or more pharmaceutically acceptable excipients comprise at least one glidant that is selected from the group consisting of calcium silicate, powdered cellulose, starch, talc, colloidal silicon dioxide, fumed silica, magnesium oxide, and magnesium silicate.

13. The composition of claim 1, wherein the cellulose ether is present in an amount ranging from about 22% (w/w) to about 28% (w/w) based on the total composition weight.

14. The composition of claim 1, wherein the cellulose ether is present in an amount ranging from about 15% (w/w) to about 21% (w/w) based on the total composition weight.

15. The composition of claim 1, wherein the cellulose ether comprises hydroxypropyl methylcellulose.

16. The composition of claim 1, wherein the hydroxypropyl methylcellulose is characterized by an apparent viscosity ranging from about 60 cP to about 140 cP when formulated as a 2% (w/w) solution in water at 20° C.

17. The composition of claim 1, wherein the hydroxypropyl methylcellulose is characterized by an apparent viscosity ranging from about 2800 cP to about 5800 cP when formulated as a 2% (w/w) solution in water at 20° C.

18. The composition of claim 1, wherein the tozadenant is present in an amount ranging from about 45% (w/w) to about 55% (w/w) based on the total composition weight.

19. The composition of claim 18, wherein the tozadenant is present in an amount of about 50% (w/w) based on the total composition weight.

20. The composition of claim 19, wherein:
the cellulose ether is present in an amount of about 25% (w/w) based on the total composition weight,
the cellulose ether consists essentially of hydroxypropyl methylcellulose, and
the hydroxypropyl methylcellulose is characterized by an apparent viscosity ranging from about 60 cP to about 140 cP when formulated as a 2% (w/w) solution in water at 20° C.

21. The composition of claim 19, wherein:
the cellulose ether is present in an amount of about 25% (w/w) based on the total composition weight,
the cellulose ether consists essentially of hydroxypropyl methylcellulose, and
the hydroxypropyl methylcellulose is characterized by an apparent viscosity ranging from about 2800 cP to about 5800 cP when formulated as a 2% (w/w) solution in water at 20° C.

22. The composition of claim 19, wherein:
the cellulose ether is present in an amount of about 18% (w/w) based on the total composition weight,
the cellulose ether consists essentially of hydroxypropyl methylcellulose, and
the hydroxypropyl methylcellulose is characterized by an apparent viscosity ranging from about 2800 cP to about 5800 cP when formulated as a 2% (w/w) solution in water at 20° C.

23. The composition of claim 1, wherein the pharmaceutically acceptable excipients are selected from the group consisting of talc, silica, isomalt, and magnesium stearate.

24. The composition of claim 1, further comprising an active agent selected from the group consisting of levodopa, carbidopa, pramipexole, ropinerole, bromocriptine, entacapone, tocapone, amantadine, and combinations thereof.

25. The composition of claim 1, comprising:
about 50% (w/w) tozadenant based on the total composition weight,
from about 2% (w/w) to about 6% (w/w) talc based on the total composition weight,
from about 0.5% (w/w) to about 1.5% (w/w) silica based on the total composition weight,
from about 16% (w/w) to about 21% (w/w) isomalt based on the total composition weight,
from about 0.25% (w/w) to about 2.5% (w/w) magnesium stearate based on the total composition weight, and
wherein the cellulose ether is characterized by an apparent viscosity ranging from about 2800 cP to about 5800 cP when formulated as a 2% (w/w) solution in water at 20° C.

26. The composition of claim 25, comprising from about 15% (w/w) to about 21% (w/w) of the cellulose ether based on the total composition weight.

27. The composition of claim 25, comprising from about 22% (w/w) to about 28% (w/w) of the cellulose ether based on the total composition weight.

28. The composition of claim 1, comprising:
about 50% (w/w) tozadenant based on the total composition weight,
from about 2% (w/w) to about 6% (w/w) talc based on the total composition weight,
from about 0.5% (w/w) to about 1.5% (w/w) silica based on the total composition weight,
from about 16% (w/w) to about 21% (w/w) isomalt based on the total composition weight,
from about 0.25% (w/w) to about 2.5% (w/w) magnesium stearate based on the total composition weight, and
from about 22% (w/w) to about 28% (w/w) of the cellulose ether based on the total composition weight,
wherein the cellulose ether is characterized by an apparent viscosity ranging from about 60 cP to about 140 cP when formulated as a 2% (w/w) solution in water at 20° C.

29. A composition comprising tozadenant, at least one cellulose ether, and one or more pharmaceutically acceptable excipients, wherein
the tozadenant is present in the composition in an amount sufficient to, when the composition is administered orally once a day for at least 14 days, provide a tozadenant $C_{ss}$ that is equivalent to the $C_{ss}$ obtained from an immediate-release formulation that is therapeutically effective when administered more than once-daily, and
the cellulose ether is present in the composition in an amount sufficient to provide a $C_{max}$ below a threshold that results in an unacceptable incidence or severity of adverse events when the composition is administered orally once a day for at least 14 days;
wherein the $C_{ss}$ is in the range of about 1.0-4.0 µg/mL;
wherein the $C_{max}$ threshold is in the range of about 2.0-5.0 µg/mL;
wherein the composition comprises from about 240 mg to about 1000 mg of tozadenant.

30. The composition of claim 29, wherein the $C_{ss}$ is in the range of about 1.0-3.0 µg/mL.

31. The composition of claim 29, wherein the $C_{max}$ threshold is in the range of about 2.0-3.5 µg/mL.

32. The composition of claim 29, wherein the composition comprises from about 240 mg to about 480 mg of tozadenant.

33. A method for treating Parkinson's disease, the method comprising administering a therapeutically effective amount of levodopa and a therapeutically effective amount of a tozadenant composition according to claim 1 to a patient in need thereof.

34. The method of claim 33, wherein the tozadenant composition is administered in an amount sufficient to reduce levodopa off-time.

* * * * *